United States Patent
Bonnet et al.

(10) Patent No.: US 7,390,875 B2
(45) Date of Patent: Jun. 24, 2008

(54) METHOD FOR BINDING, IN SOLUTION, A PEPTIDE AND A LIPOPHILIC VECTOR AND USES THEREOF

(75) Inventors: Dominique Bonnet, Lille (FR); Line Bourel, Lille (FR); Oleg Melnyk, Annoeullin (FR); Hélène Gras-Masse, Merignies (FR)

(73) Assignee: Institut Pasteur de Lille, Lille Cedex (FR)

( * ) Notice: Subject to any disclaimer, the term of this patent is extended or adjusted under 35 U.S.C. 154(b) by 801 days.

(21) Appl. No.: 10/380,094

(22) PCT Filed: Sep. 7, 2001

(86) PCT No.: PCT/FR01/02787

§ 371 (c)(1),
(2), (4) Date: May 13, 2003

(87) PCT Pub. No.: WO02/20558

PCT Pub. Date: Mar. 14, 2002

(65) Prior Publication Data

US 2004/0092015 A1 May 13, 2004

(30) Foreign Application Priority Data

Sep. 8, 2000 (FR) .................................. 00 11451

(51) Int. Cl.
C07C 47/00 (2006.01)
C07K 1/107 (2006.01)

(52) U.S. Cl. .................. 530/345; 530/410; 548/218; 552/502; 564/153; 564/159; 568/420; 568/448

(58) Field of Classification Search ................ None
See application file for complete search history.

(56) References Cited

U.S. PATENT DOCUMENTS 4,687,783 A * 8/1987 Horrmann .................... 514/693

OTHER PUBLICATIONS

Chem. Abst. 134:237782 to Fruchart, et al., Petp. New Millennium, Proc. AM. Petp. Symp., 16th (2000), Meeting Date 1999, 104-106.

(Continued)

*Primary Examiner*—Jeffrey Edwin Russel
(74) *Attorney, Agent, or Firm*—Birch, Stewart, Kolasch & Birch, LLP

(57) ABSTRACT

The invention concerns a method for binding, in solution, at least a peptide composition and at least a lipophilic vector bearing an aldehyde function, the coupling comprising a step which consists in producing a hydrazone bond between the peptide compound and the lipophilic vector. The invention also concerns lipophilic vectors for use in this method, lipopeptides obtained by this method, uses of the lipopeptides for cell screening, and the applications of the invention, in particular for preparing targeting of an active principle of the peptide kind (for example hormone or neuropeptide) through physiological barriers such as cell membranes.

27 Claims, 6 Drawing Sheets

OTHER PUBLICATIONS

Grandjean, et al., "Convergent synthesis of D-(-)-quinic and shikimic acid-containing dendrimers as potential C-lectin ligands by sulfide ligation of unprotected fragments", Journal of the Chemical Society, Perkin Transactions 1, No. 10, Oct. 1999, pp. 2967-2975.

Melnyk et al., "Synthesis of lipopeptides using hydrazone chemical ligation", Journal of Peptide Research, vol. 52, No. 9, Sep. 1998, pp. 180-184.

Shao et al., "unprotected peptides as building blocks for the synthesis of peptide dendrimers with oxime, hydrazone, and thiazolidine linkage", Journal of the American Chemical Society, vol. 117, No. 14, Apr. 12, 1995, pp. 3893-3899.

Bonnet, et al., "A novel lipophilic glyoxylic acid derivative for the lipidation of peptides using salt-free hydrazone ligation" Tetrahedron Letters, vol. 41, Dec. 2000, pp. 10003-10007.

Bonnet, et al., "Synthesis of an amphiphilic aldehyde using as a key step the condensation of a lipophilic glyoxylic acid derivative with tris (hydroxymethyl) aminomethane", Tetrahedron Letters, vol. 41, No. 10, Mar. 4, 2001, pp. 1875-1877.

* cited by examiner

SIV1: (SEQ ID NO: 1)
H-SVRPKVPLRAMTYKLAIDMSHFIKEKK(COCH$_2$NHNH$_2$)-NH$_2$

SIV2: (SEQ ID NO: 2)
H-EKGGLEGIYYSARRHRILDMYLEK(COCH$_2$NHNH$_2$)-NH$_2$

SIV3: (SEQ ID NO: 3)
H-DWQDYTSGPGIRYPKTFGWLWKLVK(COCH$_2$NHNH$_2$)-NH$_2$

SIV4: (SEQ ID NO: 4)
H-SKWDDPWGEVLAWKFDPTLAYTYEAK(COCH$_2$NHNH$_2$)-NH$_2$

SIV5: (SEQ ID NO: 5)
H-YTYEAYARYPEELEASQACQRKRLEEGK(COCH$_2$NHNH$_2$)-NH$_2$

SIV6: (SEQ ID NO: 6)
H-KFGAEVVPGFQALSEGCTPYDINQMLNCVGDK(COCH$_2$NHNH$_2$)-NH$_2$

SIV7: (SEQ ID NO: 7)
H-QIQWMYRQQNPIPVGNIYRRWIQLGLQKCVRMYNPTN-K(COCH$_2$NHNH$_2$)-NH$_2$

TT: (SEQ ID NO: 8)
Ac-QYIKANSKFIGITELKK K(COCH$_2$NHNH$_2$)-NH$_2$

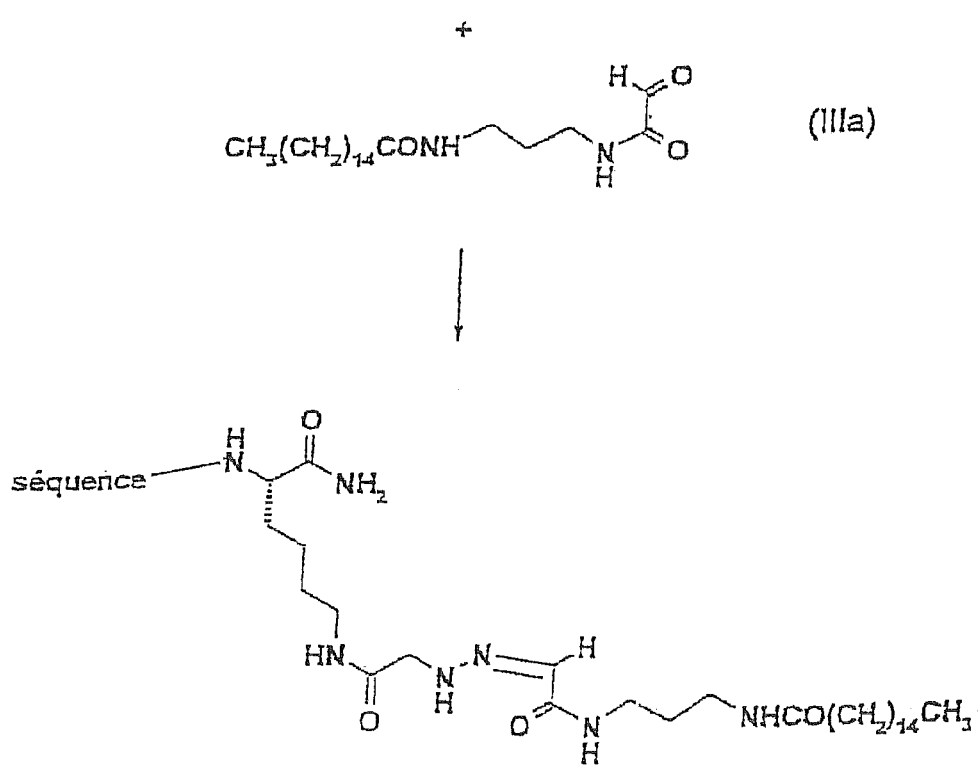

FIGURE 4

Mu-IFNγ :
H₂NNHCH₂CO-K(COCH₂NHNH₂)-AKFEVNNPQVQRQAFNELIR-
VVHQLLPESSLRKRKRSR-NH₂
(SEQ ID NO:9)
+
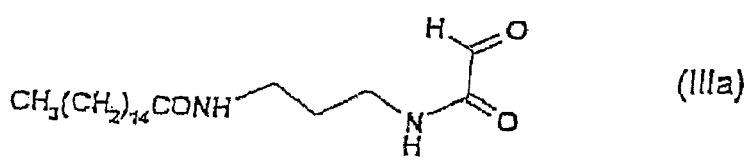  (IIIa)
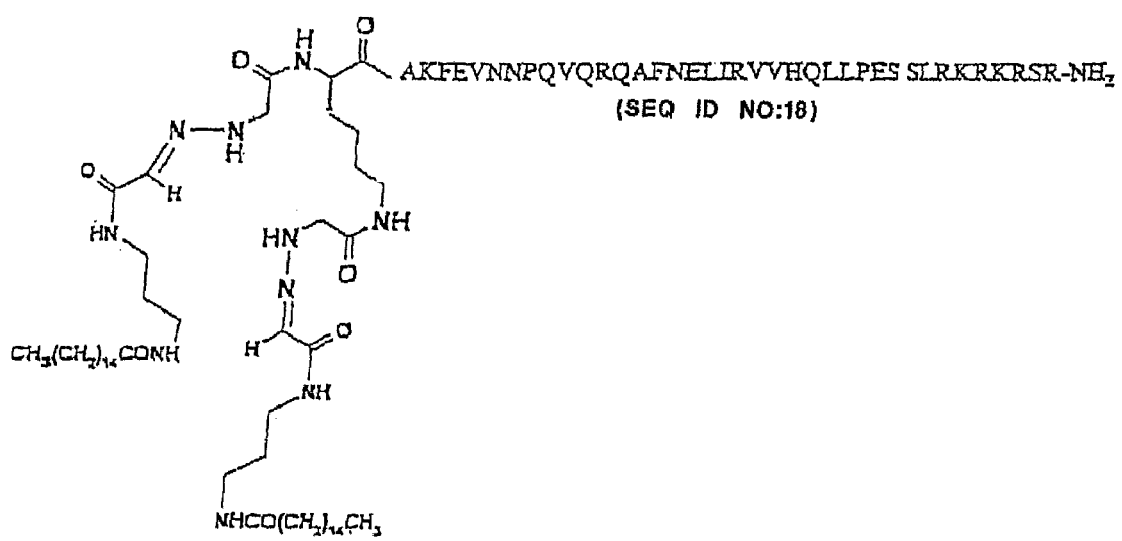
8
FIGURE 5

METHOD FOR BINDING, IN SOLUTION, A PEPTIDE AND A LIPOPHILIC VECTOR AND USES THEREOF

This application is the national phase under 35 U.S.C. § 371 of PCT International Application No. PCT/FR01/02787 which has an International filing date of Sep. 7, 2001, which designated the United States of America.

The invention relates to a process for coupling, in solution, between at least a peptide compound and at least a lipophilic vector bearing an aldehyde function, to the lipophilic vectors capable of being used in this process, to the lipopeptides thus obtained and to the applications of this process, in particular for the purpose of obtaining drugs.

The problem of introducing different substances having pharmacological properties into living cells is of major importance therapeutically. It is difficult for synthetic peptides and oligonucleotides to pass through the cell membrane. One interesting approach for improving their ability to penetrate the cell is to modify them with a lipophilic part. It has thus been demonstrated that a peptide modified by a simple aliphatic chain is capable of penetrating the cell by passive transfer through the membrane, and of interacting with its intra-cytoplasmic target. Lipopeptides are thus molecules of interest in vectorizing a functional unit within the cell.

Lipopeptides can be synthesized, for example, by coupling a fatty acid to a peptide in solid phase, as described, in particular, by K. THIAM et al. in *Biochemical and Biophysical Research Communications*, 1998, 253, 639-647 and in the *Journal of Medicinal Chemistry*, 1999, 42, 3732-3736, as well as by C. KLINGUER et al. in *Vaccine*, 2000, 18, 259-267. At the end of the synthesis, it is necessary to carry out steps involving the cleavage of the peptide/solid support bond and deprotection of the side chains of the peptide with a strong acid. This treatment considerably restricts the choice of the lipophilic part; it prevents, in particular, the use of unsaturated fatty acids. Furthermore, purification of the lipopeptides using reverse phase high-performance liquid chromatography, which is required after cleavage of the peptide/support bond is difficult to carry out and leads to low yields owing to the numerous impurities present at the end of the synthesis.

It has also been suggested coupling a protein, in solution, with a palmitoyl-coenzyme A group, the latter being introduced at the thiol group position of a cysteine. One such coupling results in the formation of a thioester link, which has the drawback of not being very stable. On the other hand, this strategy is confined to modify some proteins with the palmitoyl-coenzyme A and cannot be extended to include lipopeptide synthesis.

Current strategies for lipopeptide synthesis also consist in using chemical ligation. Chemical ligation makes it possible to bind, in solution and under extremely mild conditions, two peptide structures previously purified and completely deprotected.

It has thus been proposed binding a fatty acid to a peptide using a disulphide bond in an aqueous buffer solution. However, the disulphide bond poses numerous problems: such a link is, in fact, unstable and liable to be degraded in the presence of thiols, whence the need to prevent the solvents used to solubilize the products from being contaminated by thiols, as well the impossibility of introducing a cysteine into the peptide sequence to be vectorized. The use of thiol chemistry further makes it necessary to work in an inert atmosphere in order to avoid oxidation of the thiols.

W. ZENG et al. (*J. Pept. Sc.*, 1996, 2, 66-72) have also suggested binding, in solution, a completely deprotected, pre-purified peptide to a polyfunctional lipidic structure bound to a peptide, this being achieved via an oxime bond. The lipophilic part is introduced into a peptide sequence in solid phase, such a method having the aforementioned drawbacks, namely restriction with regard to the choice of the lipophilic part and the difficulties associated with purification of the lipidic structure.

In a similar way, O. MELNYK et al. (*J. Peptide Res.*, 1998, 52, 180-184) describe ligation, in solution and by a hydrazone bond, between a peptide bearing a lipophilic chain and an aldehyde function and another peptide the lysine side chain of which has been modified by a hydrazino group. The hydrazine bond is effected in solution but the lipophilic compound, which is of a peptide type, is solid-phase synthesized and the limitations are the same as those mentioned above.

Furthermore, C. KLINGUER et al. (*Tetrahedron Letters*, 1996, 37 40, 7259-7262) describe ligation, in a water/acetonitrile mixture, between cyclohexanecarboxaldehyde and a peptide bearing a hydrazine function. The process described by these authors does not, however, make it possible to obtain compounds that are stable, hence usable for the vectorization of active principles: the hydrazone bond formed between the hydrazine and the aldehyde is, in fact, unstable over a broad range of pH values.

Finally, D. BONNET et al. (*Tetrahedron Letters*, 2000, 41, 45-48) describe the ligation, in solution and with a hydrazide bond, of peptides functionalized by an α-hydrazinoacetic residue with activated esters of fatty acids. This method, also described in French Patent Application n° 99 10626, makes it possible to introduce complex fatty acids into peptides. However, purification using HPLC has to be carried out at the end of synthesis to separate the lipopeptide from the salts, the activation reagents and the impurities (in particular, the polyacylated peptide) present in the reaction medium. This purification is simplified by the quality of the coupling in solution, but nonetheless necessary for the reasons referred to above. This coupling process is not, therefore, suitable for the synthesis of a mixture of lipopeptides, such as those used in certain vaccines (H. GAHERY-SEGARD et al., *Journal of Virology*, 2000, 74, n° 4, 1694-1703; C. KLINGUER et al., *Vaccine, ibid*).

In view of the drawbacks of the state of the art mentioned above, the Inventors set themselves the task of providing a new strategy for the synthesis of lipopeptides and, generally speaking, of peptides modified by different compounds of a lipidic type, by chemical ligation in solution.

This new strategy of synthesis must, in particular, meet the following criteria:
 coupling of the lipidic type compound with the peptide is carried out in solution,
 coupling is carried out on the basis of/taking a completely deprotected peptide, the reaction being chemoselective/chemically selective,
 the reaction conditions of coupling permit the use of derivatives of fatty acids, including derivatives of mono and polyunsaturated complex fatty acid derivatives, and commercial derivatives of cholesterol,
 the bond formed during coupling is very stable over a wide range of pH values,
 the coupling makes it possible to obtain mixtures of lipopeptides directly usable without a prior purification step.

The Inventors also set themselves the task of providing lipopeptides capable of being obtained by chemical ligation, in which the lipid/peptide bond is very stable and does not have the drawbacks of the disulphide bond of the prior art.

These objectives are achieved through the creation of a hydrazone link between a peptide and a lipophilic vector of a non-peptide type, during convergent synthesis in solution.

The object of the invention is a process for coupling, in solution, between at least one peptide compound and at least one lipophilic vector bearing an aldehyde function, said coupling including a step of forming a hydrazone link between said peptide compound and said lipophilic vector, which process is characterized in that said lipophilic vector is of a non-peptide type and corresponds to the following general formula (I):

wherein:
i represents 0 or 1,
if i is equal to 0, D represents a bond,
if i is equal to 1, D represents a mono- or polycyclic saturated, unsaturated or aromatic heterocycle, and
$R^1$ and $R^2$, which may be identical or different, each represent a group having the formula L-f-E-f' where L represents a residue of a lipid, E represents a spacer arm, and f and f' represent functions binding, respectively, L to E and E to D.

In a particularly advantageous manner, the process according to the invention, carried out in solution, makes it possible to dispense with a step of cleavage from the support of the modified peptide compound thus obtained, which cleavage considerably restricts the choice of the lipophilic part coupled to the peptide compound, as previously mentioned.

According to one advantageous form of embodiment of the process according to the invention, this process includes the following steps:

a) preparation of at least one completely deprotected peptide compound bearing, either at its N-terminal end or at the end of the side chain of a lysine or an ornithin possibly present at some point in the peptide sequence, 1 to 4 hydrazine derivative groups having the formula —CO—CHR'—NR—$NH_2$, where R and R' represent, independently of one another, a hydrogen atom or a ramified or cyclic, linear, saturated or unsaturated alkyl group, including from 1 to 10 carbon atoms, as well as, possibly, 1 to 3 heteroatoms chosen from oxygen, sulfur, and nitrogen and substitutable by 1 to 6 groups chosen from the hydroxy, alkoxy, aryloxy, amino, aminoalkyl, aminoaryl, thio, thioalkyl, carbonyl, guanadino and carboxamido groups;

b) reaction, in solution, of said peptide compound(s) obtained in step a) with at least one lipophilic vector of a non-peptide type of formula (I) as defined above, bearing an aldehyde function.

A group derived from hydrazine, as defined hereabove, can be introduced either at the N-terminal end of the peptide or at the end of the side chain of a lysine or an ornithin possibly present at some point in the peptide sequence, by any means known to a man skilled in the art.

The hydrazine derivative groups borne by the peptide compound, mentioned in step a) of the process according to the invention are preferably α-hydrazinoacetic groups, i.e. —CO—$CH_2$—NH—$NH_2$ groups. Such groups can, for example, be introduced into the peptide compound using, for example, N,N'-tri(Boc)hydrazino-acetic acid or N,N'—-di (Boc)hydrazinoacetic acid, as disclosed in International Application PCT/FR00/02336, as well as in the article by D. BONNET et al. published in *Tetrahedron Letters*, 2000, 41, 45-48. The reaction is conducted in solid phase, the functionalized peptide then being separated from the solid support and deprotected according to methods known to a man skilled in the art.

In a particularly advantageous manner, the coupling reaction between the lipophilic vector of formula (I) and said completely deprotected peptide compound, functionalized as described above, makes it possible to dispense with any step of deprotection of the side chains of the peptide compound with a strong acid following the coupling reaction, which permits the use, as a lipophilic vector, of the sensitive fatty acid derivatives. The process according to the invention thus makes it possible to obtain directly a modified peptide compound, i.e. one coupled to a lipophilic vector.

The coupling reaction carried out during the process according to the invention (step b)), is conducted under very mild operating conditions and does not necessitate working under inert conditions, as in the case of certain processes of the prior art, in particular those that consist in coupling a peptide with a fatty acid using a disulphide bond. Coupling is efficient and rapid and is carried out under stoichiometric conditions. There are no, or only few, sub-products and precursors unconsumed, which makes it possible to obtain lipopeptides that are usable directly, without having to be purified. This is particularly advantageous insofar as lipopeptides are molecules that are difficult to purify with high-performance liquid chromatography or other methods (given problems of solubility, aggregation, etc.). In the process according to the invention, the peptide precursors can easily be purified before being coupled to the lipophilic vectors. Thus the lipopeptides obtained do not need to be purified.

Furthermore, the hydrazone bond formed, during step b) of the process according to the invention, between the aldehyde function of the lipophilic vector of formula (I) and the hydrazine derivative groups having the formula —CO—CHR'—NR—$NH_2$ borne by the peptide compound, is particularly stable, and, at all events, much more stable than a hydrazone function formed between an aldehyde and a hydrazine group (—NH—$NH_2$), a type of hydrazone bond described, in particular, by C. KLINGUER et al. (*Tetrahedron Letters*, 1996, 37, 40, 7259-7262). Indeed, the presence of the carbonyl function, in the hydrazine derivative groups borne by the peptide compounds used in the framework of the present invention, modifies the reactivity of the hydrazine function and stabilizes the hydrazone bond formed.

The reaction conducted in step b) of the process according to the invention is advantageously conducted in a mixture of water (to solubilize the peptide compound) and of at least one water-miscible lipophilic solvent (to solubilize the lipophilic vector), preferably tert-butanol.

The peptide compound implemented in the process according to the invention can be selected from the group formed by peptides and peptide derivatives, such as glycopeptides, pseudopeptides, and dendrimeric glycomimetics of the peptide type.

Within the meaning of the present invention, "peptide" is to be taken as meaning any sequence of several amino acids, whatever their nature and number; the term "peptide" thus denotes both oligopeptides (dipeptides or tripeptides) and polypeptides or proteins. "Glycopeptides" are to be taken as meaning peptides associated, by a covalent bond, with carbohydrates, whether they be monosaccharides (such as neutral oses) or polysaccharides. <<Pseudopeptides>> are to be taken as meaning peptides one or more peptide bonds (—CO—NH—) of which have been replaced by non-peptide bonds (such as —CO—NH—NH—,—$CH_2$—NH—or —CO—NH—O— bonds). <<Dendrimeric glycomimetics of a peptide type are to be taken as meaning glycomimetics the structure of which is based on amino acids or their derivatives and takes a highly ramified form, of the arborescent type.

The peptides and peptide derivatives usable in the coupling process according to the invention can advantageously present a pharmacologic activity and a therapeutic interest: they may be neuropeptides, peptides hormones or substances liable tom modulate the activity of cytokin's receptors, for example. The coupling of these peptides or peptide derivatives to a lipophilic vector, according to the process of the invention, gives them the ability to penetrate cells by transfer through the cell membrane, whatever the cells concerned.

According to one advantageous form of embodiment of the process according to the invention, the peptide compound used is a dendrimeric glycomimetic of a peptide type corresponding to general formula (II) hereinafter:

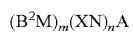  (II)

wherein:

$B^2$ corresponds to one or more general formulae (a) or (b) hereinafter

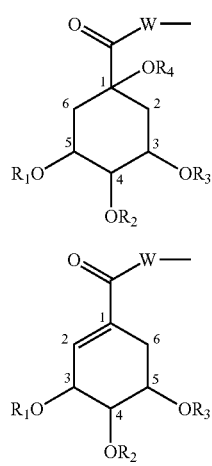

where $R_1$, $R_2$, $R_3$ and $R_4$ represent, independently of one another, a hydrogen atom or a protective group, and where W represents a bond or a saturated or unsaturated, ramified or cyclic linear carbon chain, including 1 to 18 carbon atoms and possibly 1 to 12 atoms chosen from oxygen, sulfur, and nitrogen, said carbon chain possibly being substituted by 1 to 16 halogen atoms, X represents the residue of an oligopeptide X' including 1 to 6 amino acids, A represents the residue of an at least tri-functional A' compound, m is an integer between 1 and 32, n is an integer between 0 and 32, and M and N each represent a linkage group between $B^2$ and A when n=0 or $B^2$ and X when n is other than 0, and between X and A when n is other than 0, respectively and include, independently of one another, a function chosen from among the oxime, hydrazone, amide, ester, thioester, hydrazide, hydroxamate, ether, thioether, amine, carbonate, carbamate, thiocarbonate, thiocarbamate, urea, thiourea et thiazolidine functions.

The compound of formula (II) is described in international application PCT/FR00/02194.

Within the meaning of the present invention, a <<protective>> group is to be taken as meaning a group protecting a hydroxyl function or a diol (in which case two groups chosen from $R_1$, $R_2$, $R_3$ and $R_4$ can be covalently linked to one another to form together a cycle), as defined in the work entitled *Protective Groups in Organic Synthesis*, T. W. GREENE and P. G. M. WUTS, Second Edition 1991, J. WILEY and Sons. By way of example and non-limitatively, the trimethylsilyl, triethylsilyl, triisopropylsilyl, tertiobutyldimethylsilyl, tertiobutyldiphenylsilyl, trimethylsilylethylether, tert-butoxymethyl, methoxy-methyl, benzyloxymethyl, 2-methoxyethoxymethyl, methylthiomethyl, acetyl, or 2',3'-dimethoxybutane-2',3'-diyl groups may be mentioned.

By way of example, and non-limitatively, in general formulae (a) and (b):

suitable halogen atoms are bromium, chlorine and fluorine; and suitable carbon chains are alkyl groups (methyl, ethyl, propyl, isopropyl, tertiobutyl, pentyl, etc.), alkenyl groups (vinyl, allyl, butenyl, pentenyl, etc.), alkynyl groups (ethynyl, propynyl, butynyl, pentynyl, etc.), cycloalkyl groups (cyclopentyl, cyclohexyl, etc.), heterocycles (piperazine, etc.), aryl groups (phenyl, cresyl, etc.), heteroaryl groups (pyridine, pyrimidine, pyrazine, etc.), polyethylene glycol groups or again, polyamines.

Formulae (a) and (b) represent the residues of quinic and shikimic acids and of some of their derivatives, obtained by protecting the hydroxyls borne at positions 1, 3, 4 and/or 5 in the cycle.

Compounds corresponding to general formulae (a) and (b), when they have at least two vicinal free hydroxyl functions, are mimics of D-mannose: these compounds and thus the compound of general formula (II) which bears them, are capable of being recognized by the mannose receptor and of being bound to the latter or to any receptor of the family of C-lectins related to the mannose receptor.

Compound A' is advantageously formed of a chain including several residues of an at least tri-functional compound, bound to one another by covalent bonds, and suitable for offering, at the level of the free functional groups of these residues (i.e. of the functional groups that are not involved in a covalent bond), several anchoring sites for the compound or compounds of general formula (a) and/or (b) or, when X is present, compound X'.

Compound A' preferably includes from 2 to 32 and, better still, from 4 to 16 residues of a tri-functional compound.

Preferably, compound A' includes a chain of identical or different amino acids selected from the group formed by lysine, hydroxylysine, serine, threonine, cysteine, ornithin, aspartic acid and glutamic acid. This amino acid can be either of the L series or of the D series, and compound A' can also comprise both residues of the L series and residues of the D series. A lysine-based compound A' is preferred in that it has been shown that lysine-based macromolecules are devoid of intrinsic immunogenicity (TAM, *Proc. Natl. Acad. Sci. USA*, 1988, 85, 540).

However, it is possible to use, as an A' compound, chains of tri-functional compounds other than the aforementioned amino acids, insofar as they offer satisfactory biocompatibility. By way of example, and non-limitatively, mention may be made of 3,3'-iminobis(propylamine), 2,2'-iminobis(ethylamine), gallic acid, tris(2-carboxyethyl)nitromethane (M. BRETTEICH et al., *Synlett*, 1998, 1396), tris(hydroxymethyl)aminomethane (P. R. ASHTON et al., *J. Org. Chem.*, 1998, 63, 3429) and (dihydroxy)propylamine.

Index n, which represents the number of residue X present in the compound having the general formula (II), can be:

either equal to 0, in which case residue or residues $B^2$ are directly bound to residue A, or between 1 and 32, in which case, if n is equal to 1, residue or residues $B^2$ are bound to residue A via a single residue X, whereas, if n is other than 1, each residue X can serve as a bonding element between one or more residues B² and residue A.

As to linkage groups M and N, these are chosen independently of one another, from among the linkage groups that include a function chosen from among the oxime, hydrazone, amide, ester, thioester, hydrazide, hydroxamate, ether, thioether, amine, carbonate, carbamate, thiocarbonate, thiocarbamate, urea, thiourea and thiazolidine functions. By way of non-limitative examples:

an oxime bond can be formed by reacting an O-alkylamine group with a carbonyl group, a hydrazone bond can be formed by reacting a hydrazine group with a carbonyl group, an amide (respectively, ester) bond can be formed by reacting an amine (respectively, alcohol) group with an activated acid group or anhydride or halide acid, a thioester bond can be formed by reacting a thiol group with an activated acid group or acid anhydride or halide, a hydrazide bond can be formed by reacting a hydrazine group with an activated acid group or anhydride or halide acid, an ether bond can be formed by reacting an alcohol group with an alkyl halide group, a thioether bond can be formed by reacting an alcohol group with an alkyl halide group, an amine bond can be formed by reacting an alcohol group with an alkyl halide group, a carbamate bond can be formed by reacting a chloroformate group with an alcohol group, a carbamate bond can be formed by reacting a chloroformate group with an amine group, a thiocarbonate bond can be formed by reacting a chlorothioformate group with an alcohol group, a thiocarbamate bond can be formed by reacting a chlorothioformate group with an amine group, a urea bond can be formed by reacting an isocyanate group with an amine group, a thiourea bond can be formed by reacting an isothiocyanate group with an amine group, a thiazolidine bond can be formed by reacting a β-aminothiol group with a carbonyl group, while a hydroxamate bond can be formed by reaction between an activated acid group and a hydroxylamine group.

It will thus be appreciated that, in general formula (II), B², A and X represent the residues of compounds naturally bearing functional groups suitable for leading, by reacting with one another, to the production of M and N linkage groups as defined above, or of compounds that have been modified so as to bear such functional groups.

The compound having general formula (II) is advantageously such that m is an integer of between 4 and 16, n is an integer of between 2 and 8, X represents the residue of an oligopeptide including 2 to 4 residues of amino acids, while A represents the residue of a chain including from 2 to 8 lysine residues and taking the form of a dendrimer.

The compounds having general formulae (a) and/or (b) are advantageously chosen such that the —$OR_2$ and —$OR_3$ groups are in trans relationship, so as to mimic the two hydroxyls borne by the cycle of the D-mannose which appear to be involved in the bond between this compound and its receptor.

The formula (b) compound is advantageously such that $R_1$, $R_2$ and $R_3$ represent hydrogen atoms. If, furthermore, the —OR, and —$OR_2$ groups are in cis relationship, and the —$OR_2$ and —$OR_3$ groups are in trans relationship, the configuration being 3R, 4S and 5R, the resulting compound consists of a residue of (−)-shikimic acid (or 3,4,5-trihydroxy-1-cyclohexene-1-carboxylic acid).

As to the formula (a) compound, it is advantageously such that $R_1$, $R_2$, $R_3$ and $R_4$ represent hydrogen atoms. If furthermore, the —$OR_2$ and —$OR_3$ groups are in trans relationship, while the —OR, and —$OR_4$ groups are each in cis relationship vis-à-vis the —$OR_2$ group, the configuration being $1s_n$, 3R, $4s_n$, and 5R, the resulting compound consists of a residue of the (−)-quinic acid (or 1,3,4,5-tetrahydroxy-cyclohexane-carboxylic acid).

Thus, the compound having general formula (II) is preferably such that B² represents a residue of one or more compounds chosen from among (−)shikimic acid and (−)-quinic acid, possibly in a protected form. (−)-shikimic and (−)quinic acids are commercially available, for example from the companies ALDRICH or ACROS.

The coupling process according to the invention can implement several different peptide compounds and/or several different lipophilic vectors, thus making it possible to synthesize mixtures of peptide compounds functionalized by lipophilic vectors.

Such mixtures are obtained in a single step following step b) of the process according to the invention: the use of several different peptide compounds and/or of several different lipophilic vectors in step b) leads directly to a mixture of peptide compounds functionalized by lipophilic vectors, a mixture which is directly usable, without a prior purification step nor of desalization, by direct freeze drying of the reaction medium or precipitation of the components obtained by diluting with water.

According to one advantageous form of embodiment of the coupling process according to the invention, this process implements, in step b), at least one lipophilic vector bearing an aldehyde function, at least one peptide compound chosen from among peptides, glycopeptides and pseudopeptides, as well as at least one dendrimeric glycomimetic having the general formula (II) as defined above.

The use of at least one compound having formula (II) during step b) of the coupling according to the invention advantageously leads to the production of a mixture including at least one peptide compound chosen from among peptides, glycopeptides and pseudopeptides, and at least one dendrimeric glycomimetic having formula (II), each being respectively linked to one or more lipophilic vectors. By reason of the presence of lipophilic chains, said mixture is organized in the form of mixed micelles. Owing to the presence of the formula (II) compound in these micelles, said peptide compounds can be selectively vectorized towards cells possessing mannose receptors or receptors of the C-lectins family related to the mannose receptor.

The invention also relates to a lipophilic vector usable in the coupling process defined hereabove, characterized in that it corresponds to general formula (I):

$$[(R^1)(R^2)_i]D\text{—CHO} \qquad (I)$$

as defined previously.

Such a lipophilic vector is advantageously such that i is equal to 1 and D represents the heterocycle 1-aza-3,7-dioxabicyclo (3.3.0)-octane.

Group L (in the formula L-f-E-f' defined in relation to $R^1$ and $R^2$) represents, for example, a sterol, a sterol derivative (such as a cholesterol derivative) or a linear or ramified, saturated or unsaturated carbon chain, including between 4 and 30 carbon atoms. Such a carbon chain constitutes the lipophilic part of a fatty acid, such as palmitic acid (when L corresponds to the formula $CH_3—(CH_2)_{14}—$) or oleic acid (when L corresponds to the formula $CH_3—(CH_2)_7—CH=CH—(CH_2)_7—$).

Furthermore, E advantageously represents a saturated or unsaturated, linear, ramified or cyclic carbon chain, comprising 1 to 18 carbon atoms and, optionnaly, 1 to 16 heteroatoms (for example nitrogen or oxygen) and/or 1 to 7 groups selected from among the carbonyl groups, heterocycles, heteroaryls, carbocycles and aryls. E may possibly be substituted by 1 to 8 hydroxyl or amino groups and/or 1 to 16 halide atoms (such as chlorine or fluorine).

Within the meaning of the present invention:
- <<carbocycle>> (also called (<<cycloalkyl>>) is to be taken as meaning a mono- or polycyclic carbon cycle including between 3 and 8 carbon atoms, such as cyclopentyl or cyclohexyl;
- <<aryl>> is to be taken as meaning a mono- or polycyclic aromatic carbon cycle including between 5 and 14 carbon atoms, such as phenyl, naphtyl or cresyl;
- <<heterocycle>> is to be taken as meaning a carbocycle including one or more heteroatoms chosen from among nitrogen, oxygen and sulfur, such as piperazine;
- <<heteroaryl>> is to be taken as meaning an aryl including one or more heteroatoms chosen from among nitrogen, oxygen and sulfur, such as pyridine, pyrimidine or pyrazine.

As to f and f', these functions represent, for example, a —CO—NH— or —CO—O— and —NH—CO— or —O—CO— bond, respectively.

Examples of preferred lipophilic vectors according to the invention correspond to formulae (III) and (IV) hereinafter:

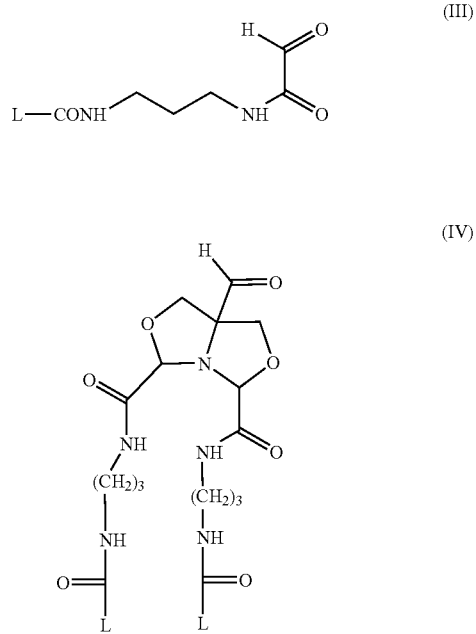

wherein L is as defined previously and represents, for example:
- in formulae III and IV, a carbon chain having the formula $CH_3—(CH_2)_{14}—$ (i.e. the lipophilic part of palmitic acid) or a carbon chain having the formula $CH_3—(CH_2)_7—CH=CH—(CH_2)_7$ (i.e. the lipophilic part of oleic acid), in formula III, a carbon chain having the formula $CH_3—(CH_2)_7—CH=CH—(CH_2)_7—$ (i.e. the lipophilic part of oleic acid), or a sterol derivative.

The lipophilic vectors according to the invention are particularly suitable for use as such, and without any prior activation being necessary, in the coupling process defined previously.

The invention also relates to a lipopeptide that can be obtained using the coupling process as defined above, characterized in that it is essentially constituted by at least one peptide compound bound, via a hydrazone bond, to at least one lipophilic vector of a non peptide type of formula (I) as defined hereabove. Said peptide compound is advantageously as defined previously in relation to the coupling process according to the invention.

As mentioned earlier, such a lipopeptide has the ability of penetrating the cells by passive transfer through the cell membrane, in a non-selective manner.

The invention also relates to a mixture of several different lipopeptides as defined above. Such a mixture can be obtained with the coupling process according to the invention as previously described.

The invention also relates to the use of a lipopeptide as defined above for cell targeting.

The invention also relates to the use of a coupling process defined above for the preparation of a drug including at least one active principle of a peptide type vectorized by at least one lipophilic compound, useful for cell targeting.

In such a drug, the peptide type active principle (for example an antigen, a hormone or a neuropeptide), vectorized by a lipophilic compound, is capable of passing through lipophilic physiological barriers, such as cell membranes, in a non-selective manner (that is so say whatever the cells concerned). The physical properties of the active principle are thus modified since the active principle, through the presence of lipophilic chains, takes the form of micelles or aggregates, which make it possible, in particular, in the case of mixed micelles, to group together peptides of different types in a same environment. When these micelles or aggregates also include a compound of formula (II) bound, via a hydrazone bond, to at least one lipophilic vector, the resulting drug makes it possible to target the receptors of the family of C-lectins related to the mannose receptor.

In addition to the preceding provisions, the invention includes yet others which will emerge from the description that follows, which refers to examples of implementation of the process according to the present invention and of synthesis of lipopeptides according to the present invention, as well as to the annexed drawings, wherein:

FIG. 4 illustrates the coupling, using the process according to the invention, of a mixture of peptides referred to as SIV1-7 (SEQ ID NO: 7) and TT (SEQ ID NO: 8) with a lipophilic vector of formula (IIIa);

FIG. 5 illustrates the coupling, using the process according to the invention, of the peptide referred to as Mu-IFNγ (SEQ ID NO: 9) with two lipophilic vectors of formula (IIIa);

Figure 1:
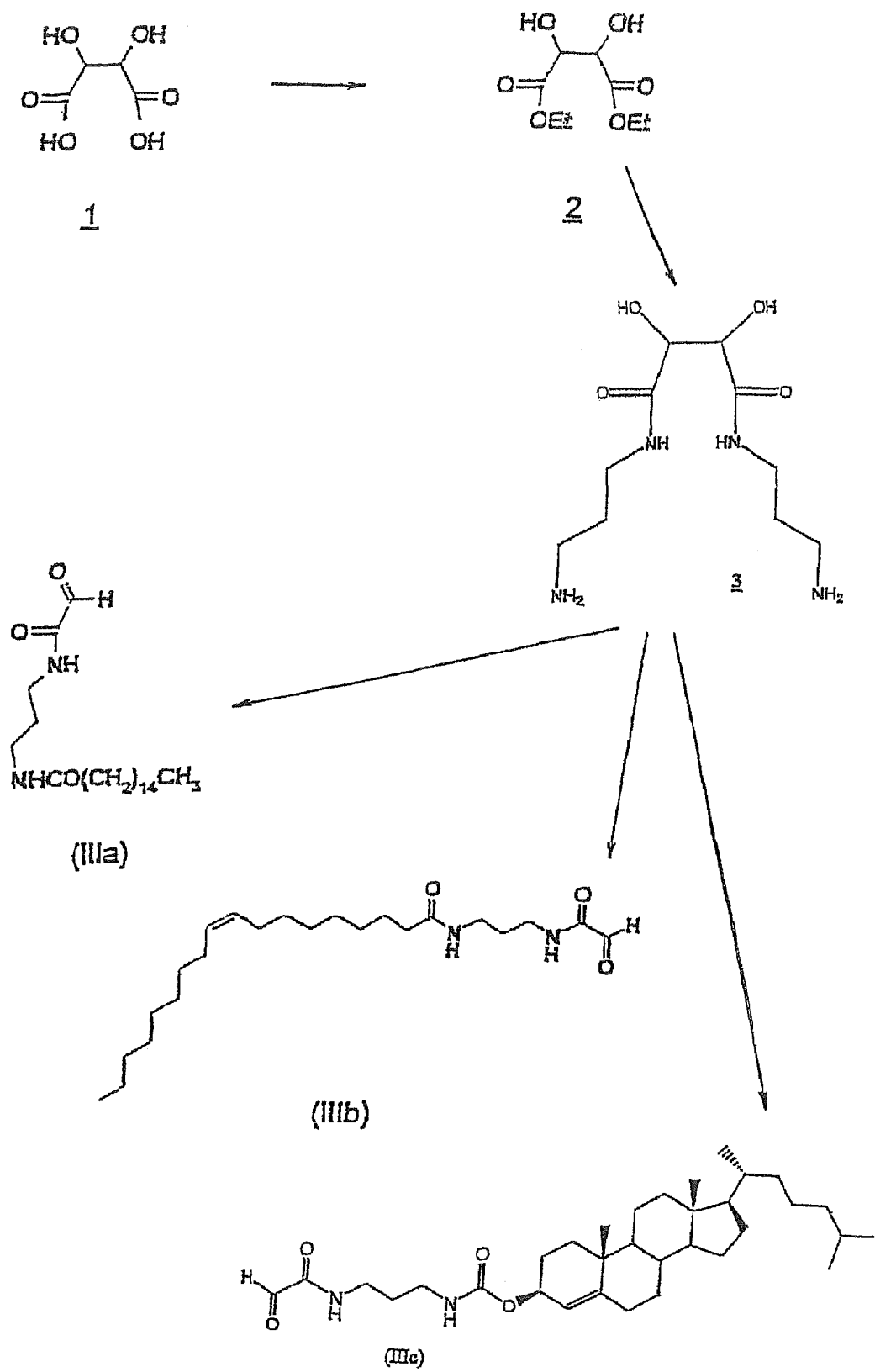
FIG. 1 illustrates the synthesis of the lipophilic vectors of formulae (IIIa) and (IIIb) according to the invention.

It should be clearly understood, however, that these examples are given solely by way of illustration of the object of the invention, of which they are in no way limitative.

In the examples that follow, the following abbreviations are used: eq.: equivalents; Boc: tert-butyloxycarbonyl ; Fmoc: 9-fluorenyl-methoxycarbonyl; Mtt: 4-methyl-trityl DMF: dimethylformamide; TFA: trifluoroacetic acid; $CH_2Cl_2$: dichloromethane; MeOH: methanol; EtOH: ethanol; THF: tetrahydrofuran; AcOH: acetic acid; AcOEt: ethyl acetate; $H_2O$: water; $AcO^-NH_4^+$: ammonium acetate; $CDCl_3$: deuterated chloroform; EDT: ethanedithiol; TIS: triisopropylsilane; DMSO-d6: dimethylsulfoxide-d6 (fully deuterated); $NaIO_4$: sodium periodate; NaCl: sodium chloride ; $Na_2SO_4$: sodium sulfate ; $MgSO_4$: magnesium sulfate; $KH_2PO_4$: potassium dihydrogen phosphate; PAL: <<peptideamide linker >>; BOP: benzotriazol-1-yl-oxytris(dimethylamino)phosphoniumhexafluorophosphate; HOBt: N-hydroxybenzotriazol; HBTU: N-[(1H-benzotriazol-1-yl)(dimethylamino)methylene]-N-methyl methanaminium hexafluorophosphate N-oxide; DIEA: diisopropylethylamine; TEAP: triethylamine phosphate; HPLC: high-performance liquid chromatography; RP-HPLC: reverse phase high-performance liquid chromatography; ES-MS: electrospray mass spectrometry; TOF-PDMS: plasma desorption mass spectrometry; LC-MS: mass spectrometry coupled with analysis using liquid chromatography; NMR $^1$H: proton nuclear magnetic resonance; NMR $^{13}$C : carbon nuclear magnetic resonance.

EXAMPLE 1

Synthesis of peptides functionalized by α-hydrazinoacetic groups

The following peptides, functionalized by α-hydrazinoacetic groups either at their N-terminal ends or at the end of the side chain of a lysine (K) present in the peptide sequence, were prepared (SEQ ID NOS: 1-11 and 14-15):

```
SIV1:       H-SVRPKVPLRAMTYKLAIDMSHFIKEKK(COCH2NHNH2)-NH2
            (SEQ ID NO: 1)

SIV2:       H-EKGGLEGIYYSARRHRILDMYLEK(COCH2NHNH2)-NH2
            (SEQ ID NO: 2)

SIV3:       H-DWQDYTSGPGIRYPKTFGWLWKLVK(COCH2NHNH2)-NH2
            (SEQ ID NO: 3)

SIV4:       H-SKWDDPWGEVLAWKFDPTLAYTYEAK(COCH2NHNH2)-NH2
            (SEQ ID NO: 4)

SIV5:       H-YTYEAYARYPEELEASQACQRKRLEEGK(COCH2NHNH-2)-NH2
            (SEQ ID NO: 5)

SIV6:       H-KFGAEVVPGFQALSEGCTPYDINQMLNCVGDK(COCH2NHNH2)-NH2
            (SEQ ID NO: 6)

SIV7:       H-QIQWMYRQQNPIPVGNIYRRWIQLGLQKCVRMYNPTN-
            K(COCH2NHNH2)-NH2
            (SEQ ID NO: 7)

TT:         Ac-QYIKANSKFIGITELKK K(COCH2NHNH2)-NH2
            (SEQ ID NO: 8)

Mu-IFNγ:    H2NNHCH2CO-K(COCH2NHNH2)-AKFEVNNPQVQRQAFNELIR-
            VVHQLLPESSLRKRKRSR-NH2 (SEQ ID NO: 9)

Mu-IFNγ a:  H-K(COCH2NHNH2)IRVVHQLLPESSLRKRKRSR-NH2
            (SEQ ID NO: 10)

Mu-IFNγ b:  H-K(COCH2NHNH2)SLRSERRHQKVRPIRVLSKL-NH2
            (SEQ ID NO: 11)

Mu-IFNγ c:  H-K(COCH2NHNH2)AKFEVNNPQVQRQAFNELIRVVHQLLPESSLRKRKRSR-NH2
            (SEQ ID NO: 12)

Mu-IFNγ d:  H-K(COCH2PSRENQNAVKIQKLSVVLRREQKHRVERLAFRNQSLPF-NH2
            (SEQ ID NO: 13)

OVA:        Ac-K(COCH2NHNH2)-ISQAVHAAHAEINEAGR-NH2
            (SEQ ID NO: 14)

G18R:       H-K(COCH2NHNH2)GAVVGGLGGYMLGSAMSR-NH2
            (SEQ ID NO: 15)
```

These hydrazinopeptides are solid-phase synthesized according to the protocols described hereinafter.

1) Preparation of the Fmoc-Lys(Boc$_2$NN(Boc)CH$_2$CO)-PAL-PEG-PS resin.

The starting resin is the Fmoc-PAL-PEG-PS resin with 0.16 mmol/g filler (Perseptive Biosystems, 25 g). It is treated with piperidine 20% in DMF. The amino acid Fmoc-Lys (Mtt)-OH (Senn Chemicals), used in the proportion of 4 eq. in relation to the reactive amino acids present in the solid support, is activated by the HBTU/HOBt/DIEA mixture (4 eq./4 eq./8 eq.) in the DMF for 1 minute. The activated acid is then added to the resin. After stirring for 1 hour, the resin is washed with DMF and then with $CH_2Cl_2$ and stored in $CH_2Cl_2$ at 4° C.

The Mtt group is deprotected by a series of washing operations with TFA 1% in $CH_2Cl_2$. That deprotection is followed by RP-HPLC on a TSK column, (with) Super-ODS gel (Tosohaas). Deprotection is completed after 13 to 16 washing operations. The resin is neutralized by washing twice with diisopropylethylamine 5% in $CH_2Cl_2$, and then washed with $CH_2Cl_2$.

Coupling of the N,N'-tri(Boc)hydrazinoacetic acid, which is conducted as disclosed in international application PCT/FR00/02336, is effected using 1.2 eq. of N,N'-tri(Boc)hydrazinoacetic acid in relation to the reactive amino functions present on the solid support. The N,N'-tri(Boc)hydrazinoacetic acid is activated using a mixture of BOP/DIEA (M. GAIRI et al., *Tetrahedron Letters,* 1990, 50, 7363) or HBTU/HOBt/DIEA in DMF (N,N'-tri(Boc)-hydrazino-acetic acid/BOP/DIEA: 1/1/3, or N,N'-tri(Boc)hydrazino-acetic acid/HBTU/HOBt/DIEA: 1/1/1/3), and then added in a single operation to the solid support in suspension in the DMF. After 30 minutes, the support is washed with DMF and $CH_2Cl_2$.

The Fmoc-Lys(Boc$_2$NN(Boc)CH$_2$CO)-PAL-PEG-PS resin thus prepared is used directly for peptide synthesis on a support.

2) Synthesis of Peptides SIV1 to SIV7 and TT.

Synthesis protocol.

Hydrazinopeptides SIV1-7 and TT are solid-phase synthesized on Fmoc-Lys(Boc$_2$NN(Boc)CH$_2$CO)-PAL-PEG-PS resin using the Fmoc/tert-butyl chemistry, as described, for example, in <<*Fmoc solid phase peptide synthesis, a practical approach*>> (W. C. CHAN & P. D. WHITE Editors, Oxford University Press, Oxford 2000) or by G. B. FIELDS et al. in *Int. J. Pept. Protein,* 1990, 35, 161, with HBTU/HOBt activation (M. SCHNÖLZER et al., *Int. J. Pept. Protein Res.,* 1992, 40, 180). The synthesis is carried out on a Pioneer automatic synthesizer (Perseptive Biosystems). The synthesis reagents are as follows:

deprotection of the amine functions: piperidine 20% in DMF, activator of the amino acids: HBTU/HOBt (the two reagents being used in a concentration of 0.5 M in DMF, solution of DIEA, 1M in DMF, <<capping>> solution (i.e. blocking the reactive functions that have not reacted): acetic anhydride 3% and DIEA 0,3% in DMF.

Hydrazinopeptides SIV1 and SIV2 were synthesized on a scale of 0.1 mmole, using 10 equivalents of amino acids. As to peptides SIV3 to SIV7 and TT, these were synthesized on a scale of 0.25 mmole using 4 equivalents of amino acids. The syntheses were carried out in double coupling with <<capping>>, in the following succession of steps: deprotection of the amine function, activation of the amino acid and coupling (twice), followed by <<capping>> with the acetic anhydride solution.

Cleavage and deprotection of hydrazinopeptides SIV1-7 and TT.

The hydrazinopeptides are cleft from the solid support and simultaneously deprotected, through the action of the TFA in the presence of carbo-cation traps. The mixture used is as follows:

in the case of peptides SIV1 and SIV2: TFA 95%, TIS 2.5%, $H_2O$ 2.5%, in the case of peptide SIV4: TFA 95%, EDT 2.5%, $H_2O$ 2.5%, in the case of peptides SIV3, SIV5, SIV6, SIV7 and TT: TFA/EDT/thioanisole/$H_2O$/phenol (10 ml/0.25 ml/0.5 ml/0.5 ml/0.75 g).

The duration of the cleavage reaction of the hydrazinopeptides from the solid support varies between 1½ hours and 2½ hours with stirring. The peptides are then precipitated in cold ethyl ether and centrifuged.

Purification of hydrazinopeptides SIV1-7 and TT.

The hydrazinopeptides are purified by RP-HPLC on a preparative column (15 mm. in diameter and 500 mm long) with a C3 stationary phase (Zorbax) on a Shimadzu 6A HPLC chain equipped with a Kipp&Zonen plotting table and a Gilson fraction collector. The eluting solvents (solvents A and B) are as follows:

solvent A: deionized water including 0.05% of TFA, solvent B: isopropanol 40% in dionized water including 0.05% of TFA (in the case of peptides SIV4 and SIV5), or n-propanol 40% in deionized water including 0.05% of TFA (in that of the other peptides).

The raw hydrazinopeptides are placed in solution in a 10 to 20 mg/ml water/acetic acid mixture for injected quantities ranging from 40 to 80 mg, depending on the peptide. The purification gradients vary according to the hydrazinopeptides injected:

SIV1: from 15 to 40% of buffer solution B in 25 minutes (4 ml/min, 50° C.),

SIV2: from 15 to 30% of buffer solution B in 30 minutes (3 ml/min, 50° C.),

SIV3: from 20 to 40% of buffer solution B in 20 minutes (3 ml/min, 50° C.),

SIV4: from 20 to 50% of buffer solution B in 30 minutes (3 ml/min, 50° C.),

SIV5: from 15 to 30% of buffer solution B in 15 minutes (3 ml/min, 50° C.),

SIV6: from 30 to 60% of buffer solution B in 25 minutes (3 ml/min, 50° C.),

SIV7: from 30 to 40% of buffer solution B in 30 minutes (3 ml/min, 50° C.),

TT: from 0 to 25% of buffer solution B in 25 minutes (3 ml/min, 50° C.).

UV detection is carried out at 225 nm, except in the case of SIV7, for which detection is carried out at 280 nm. The collected fractions are analyzed using RP-HPLC (Shimadzu 10A chain/system) on a C3 column (Zorbax, 4.6 mm in diameter, 160 mm long) with a linear gradient of 0 to 100% of buffer solution B in 30 minutes (detection at 215 nm, flow rate: 1 ml/min, 50° C.). The fractions containing the hydrazinopeptides are gathered together and freeze dried.

Table I collects together, for hydrazinopeptides SIV1 to SIV7 and TT, the weights of raw peptides obtained after synthesis, the weights of purified peptides obtained after purification using RP-HPLC, as well as the purity percentage of these purified peptides.

TABLE I

|  | Raw peptide (mg) | Purified peptide (mg) | Purity (%) |
|---|---|---|---|
| SIV1 | 284 | 35 | 100 |
| SIV2 | 251 | 42 | 93 |
| SIV3 | 365 | 68 | 90 |
| SIV4 | 532 | 141 | 99 |
| SIV5 | 661 | 48 | 93 |
| SIV6 | 637 | 148 | 98 |
| SIV7 | 776 | 68 | 82 |
| TT | 434 | 120 | 97 |

Analysis of hydrazinopeptides SIV1-7 and TT.

In order to confirm their identity, the purified hydrazinopeptides are analysed by ES-MS using a Micromass Quatro spectrometer. The molecular weights calculated (<<calc. >>) and observed (<<obs. >>) are as follows: SIV1 calc. 3258.9, obs. 3257.5; SIV2 calc. 2969.35, obs. 2968; SIV3 calc. 3113.5, obs. 3111.5; SIV4 calc. 3188.5, obs. 3187; SIV5 calc. 3453.7, obs. 3452.5; SIV6 calc. 3502.9, obs. 3501.5; SIV7 calc.4806.5, obs. 4804.5; TT calc. 2222.57, obs. 2220.5.

The hydrazinopeptides are also analyzed using capillary electrophoresis (Applied Biosystems 270A-HT). The operating conditions are as follows:

SIV4, SIV5 and SIV6: borate buffer, 50 mM, 30 kV, 10 minutes, 200 nm, 45° C., injection for 1.5 seconds, in the case of the other hydrazinopeptides: citric acid buffer solution, 20 mM, pH 2,1, 30 kV, 10 minutes, 200 nm, 45° C., injection for 1.5 seconds.

The hydrazinopeptides are further subjected to an analysis of the amino acids composition after total acid hydrolysis with hydrochloric acid 6N, for 24 hours and at 110° C. Apart from providing a third confirmation of their identity, this analysis makes it possible to estimate the percentage of peptide in the freeze dried product. The results of this analysis are as follows : SIV1: 91.9%; SIV2: 78.2%; SIV3: 97.9%; SIV4: 100%; SIV5: 92.7%; SIV6: 74.9%; SIV7: 95.1%; TT: 100%.

3) Synthesis of Peptides Mu-IFNγ, Mu-IFNγ a, Mu-IFNγ b, Mu-IFNγ c and Mu-IFNγ d.

The sequences present in peptides Mu-IFNγ and Mu-IFNγ c on the one hand, and Mu-IFNγ a, on the other hand, correspond respectively to the 38 and the 20 contiguous amino acids at the C-terminal end of the murine interferon-γ (IFN-γ), as described, in particular, in the international PCT application published under the number WO 99/40113, and by K. THIAM et al. in *Biochemical and Biophysical Research Communications*, 1998, 253, 639-647 and in the *Journal of Medicinal Chemistry*, 1999, 42, 3732-3736. As to the sequence present in peptide Mu-IFNγ b and Mu-IFNγ d, this is <<scramble>> sequences of the one present in peptide Mu-IFNγ a and Mu-IFNγ d, respectively, i.e. sequences in which the order of the amino acids has been arranged so as to avoid any sequential relationship with the original peptide. Such a peptide will serve as a control (peptide) in the biological tests to be described below.

Synthesis of hydrazinopeptide Mu-IFNγ.

Hydrazinopeptide Mu-IFNγ is prepared using 0.25 mmole of a Rink amide resin MBHA PS of 0,74 mmol/g filler (Applied Biosystems, Foster City, USA), according to the Fmoc/tert-butyl strategy (as described above in connection with the synthesis of hydrazinopeptides SIV1 to SIV7 and TT) and conventional activation using an Applied Biosystems 430 A peptide synthesizer. At the end of synthesis, part of the peptidyl-resin (31.25, μmoles) is modified at the N-terminal end by a Fmoc-L-Lys(Fmoc)—OH group. After displacement of the Fmoc groups by a solution of piperidine 20% in DMF, the N,N'-tri(Boc)hydrazino-acetic acid (36.48 mg, 1.2 eq. per amino group) is introduced manually using BOP activation in situ, as described in 1) above.

The cleavage and deprotection of hydrazinopeptide Mu-IFNγ is carried out in the presence of a TFA/H$_2$O/phenol/EDT/thioanisole mixture (1 g of dry resin/10.0 ml of TFA/0.5 ml of water /0.75 g of phenol/0.25 ml of EDT/0.5 ml of thioanisole). After precipitation in an ether/heptane mixture (1/1 by volume) and centrifuging, the peptide is recovered in a water/acetic acid mixture (80/20 by volume), frozen and freeze dried.

Hydrazinopeptide Mu-IFNγ is purified using RP-HPLC in a preparative column (15 mm in diameter and 300 mm long) with a C3 stationary phase (Zorbax), as described in the case of purification of hydrazinopeptides SV1 to SV7 and TT. The elution flow rate is 3 ml/minute using a gradient of 25 to 90% of solvent B (isopropanol 40% in deionized water including 0.05% of TFA) in solvent A (deionized water including 0.05% of TFA). After freeze drying, hydrazinopeptide Mu-IFNγ (16.1 mg, yield 8.5%) is stored at −20° C. Its ES-MS analysis is as follows: [M+H]$^+$ calculated 4846.6; found 4845.5.

Synthesis of hydrazinopeptides Mu-IFNγ a and Mu-IFNγ b.

The procedure is the same as for synthesis of hydrazinopeptide Mu-IFNγ. After the cleavage and deprotection stages, the peptides are precipitated in ethyl ether, centrifuged, recovered in a water/acetic acid mixture (90/10 by volume), frozen and freeze dried. 430 mg and 594.4 mg of peptides Mu-IFNγ a and Mu-IFNγ b in raw form are obtained respectively. The peptides are purified as described above in the case of peptide Mu-IFNγ, using a gradient of 0 to 50% of solvent B in 50 minutes. There are thus obtained, respectively, 61.4 mg and 104.2 mg of purified peptides Mu-IFNγ a and Mu-IFNγ b. Mu-IFNγ a: TOF-PDMS [M+H]$^{30}$ calculated 2659.22; found 2660.9. Mu-IFNγ b : ES-MS [M+H]$^{30}$ calculated 2658.22; found 2657.0.

Synthesis of hydrazinopeptides Mu-IFNγ c and Mu-IFNγ d.

Hydrazinopeptides Mu-IFNγ c and Mu-IFNγ d are prepared using 0.1 mmole of a Fmoc-PAL-PEG-PS resin (Perseptive Biosystems), according to the Fmoc/tert-butyl strategy (as described above in the case of synthesis of hydrazinopeptides SIV1 to SIV7 and TT) and active classification using a Pioneer peptide synthesizer (Perseptive Biosystems). The syntheses are carried out using single coupling and an amino acid excess of 10 in relation to the theoretical load of the peptidyl-resin. At the end of synthesis the peptidyl-resins are modified at the N-terminal end by a Boc-L-Lys(Fmoc)—OH residue. After displacement of the Fmoc group by a solution of piperidine 20% in DMF, the N,N'-tri(Boc)hydrazino-acetic acid (390 mg, 10 equivalents) is also introduced automatically. The cleavage and deprotection steps are carried out as described above in connection with the preparation of the Mu-IFNγ. Purification of peptides Mu-IFNγ c and Mu-IFNγ d is carried out as described above in the case of peptide Mu-IFNγ, using, respectively, a gradient of 25 to 100% of buffer solution B in 75 minutes and of 20 to 100% of buffer solution B in 80 minutes.

158 mg (26%) of peptide Mu-IFNγ c are thus obtained after freeze drying. ES-MS calculated 4772.6; found 4771.5: m/z 1193.5 [M+4H]$^{4+}$, 955.1 [M+5H]$^{5+}$, 796.0 [M+6H]$^{6+}$, 682.2 [M+7H]$^{7+}$.

120 mg (20%) of peptide Mu-IFNγ d are thus obtained after freeze drying. ES-MS calculated 4772.6; found 4771.0; m/z 1193.7, [M+4H]$^{4+}$, 955.3 [M+5H]$^{5+}$, 796.2 [M+6H]$^{6+}$, 682.5 [M+7H]$^{7+}$.

4) Synthesis of Peptide OVA.

Hydrazinopeptide OVA is solid-phase synthesized using 0.10 mmole of a Fmoc-PAL-PEG-PS resin of 0.16 mmol/g filler (Perseptive Biosystems), using Fmoc/tert-butyl chemistry and HBTU/HOBt activation, as described above in the case of synthesis of hydrazinopeptides SIV1 to SIV7 and TT, using a Pioneer peptide synthesizer. At the end of synthesis, the α-$NH_2$ function of the lysine is treated for 20 minutes in the presence of piperidine 20% in DMF, and then acetylated for 10 minutes using a solution of acetic anhydride 10% in $CH_2Cl_2$. Protective group Mtt of the ε-$NH_2$ function of the lysine is displaced using a solution of TFA 1% in $CH_2Cl_2$. 13 cycles including, each time, treatment with 20 ml of this solution are necessary. Finally, the resin is washed twice, for 2 minutes, with 20 ml of $CH_2Cl_2$.

The N,N'-tri(Boc)hydrazinoacetic acid (47 mg, 0.12 mmole) is then coupled to the ε-$NH_2$ function of the lysine using HBTU/HOBt/DIEA activation (1.12 mmole/0.12 mmole/0.24 mmole) for 60 minutes, as described above in connection with the synthesis of hydrazinopeptides SIV1 to SIV7 and TT. After the peptidyl-resin has been washed and dried, it is treated in the presence of 95% TFA/2.5% $H_2O$/2.5% TIS (as described above in connection with the cleavage and deprotection of hydrazinopeptides SIV1 and SIV2) for 2 hours at room temperature. The hydrazinopeptide is finally precipitated, dissolved in a water/acetic acid mixture, frozen and then freeze dried.

Hydrazinopeptide OVA thus obtained in raw form is purified on a Zorbax C3 column. The elution flow rate is 4 ml/minute using a linear gradient of 0 to 20%, in 20 minutes, of a dionized water /isopropanol mixture (2/3) including 0.05% of TFA in a dionized water/0.05% TFA mixture. After freeze drying, 74 mg (yield 30%) of hydrazinopeptide OVA are obtained. The analysis of peptide OVA using ES-MS is as follows: $[M+H]^+$ calculated 2016.1; found 2015.0.

5) Synthesis of Peptide G18R.

Synthesis is carried out using a Pioneer automatic synthesizer (Perseptive Biosystems) with 0.2 mmole of Fmoc-PAL-PEG-PS resin, according to the protocol described above in connection with the synthesis of peptides SIV1-7 and TT. The steps of cleavage and deprotection are carried out using a TFA/TIS/$H_2O$/EDT mixture (94%/1%2,5%/2.5% by volume). After precipitation in ethyl ether, 360 mg of raw peptide are obtained. This peptide is purified on a Zorbax C3 column, with an elution flow rate of 4 ml/minute using a linear gradient of 0 to 30%, in 30 minutes, of a deionized water/isopropanol mixture (40% by volume) including 0.05% of TFA in a deionized water/0.05% TFA mixture. After freeze drying, 117 mg of hydrazinopeptide G18R are obtained. Its analysis using TOF-PDMS is as follows: $[M+H]^+$ calculated 1883.2; found 1881.1.

EXAMPLE 2

Synthesis of Tetraquinoylated Lysine Tree Bearing a Hydrazino Group, According to General Formula (II)

[$(Qui)_4AKHdz$]

The $(Qui)_4AKHdz$ tree is prepared on a scale of 0.125 mmole from an amide Rink resin Nleu AM-PS, of 0.75 mmole/g filler according to the Fmoc/tert-butyl strategy (as described above in the case of synthesis of hydrazinopeptides Mu-IFNγ). The synthesis is carried out manually using an amino acid excess of 4 in relation to the reactive amino groups present on the solid support and HBTU/HOBt/DIEA activation, 4/4/8 equivalents (M. SCHNÖLZER et al., Int. *J. Pept. Protein Res.*, 1992, 40, 180), using DMF as the solvent. The Fmoc-β-Ala—OH is first coupled to the resin, followed by the first lysine residue in the form of the compound Fmoc-L-Lys(Mtt)—OH. The 4-methyltrityl group (Mtt) is eliminated by treating with a 1% trifluoroacetic acid solution in dichloromethane as described in L. BOUREL et al., *J. Peptide Sci.*, 2000, 6, 264). The N,N'-tri(Boc)hydrazinoacetic acid is then coupled to the amino function of the side chain (using an excess of 1.2 equivalent per reactive amino function) after pre-activation using an HBTU/HOBt/DIEA mixture, 1.2/1.2/2.4, in DMF. Preparation of the tree is continued by coupling one, and then two, lysines in the form of their Fmoc-L-Lys (Fmoc)—OH derivatives. The two coupling stages are each followed by a "capping" step (i.e. blocking of any amino functions that have not reacted), by treating the peptidyl-resin with an $Ac_2O$/DIEA/$CH_2Cl_2$ mixture (10/5/85) for 5 minutes. After removal of the Fmoc groups by treatment with a 20% piperadine solution in DMF for 20 minutes, the peptidyl-resin is reacted with ($1s_n$,3R,$4s_n$,5R)-1,3,3,5-tetra-acetoxycyclohexane-1-carboxylic acid (2 and 4 equivalents in relation to the reactive amino functions) activated in situ by a PyBOP/DIEA mixture (2 and 4 equivalents in relation to the reactive amino functions, respectively) in DMF. The coupling is repeated using the same reagents in a proportion of 1/1/2 equivalents in relation to the initial reactive amino functions. The resin is then washed with dichloromethane (3×2 minutes) and then ethyl ether (2×1 minute) and then dried.

The peptidyl-resin is then treated with a TFA/TIS/$H_2O$ mixture (95/2.5/2.5) (6 ml) for 1 hour, 30 minutes at room temperature. The raw product of cleavage is precipitated after filtering in a cooled mixture of ethyl ether/heptane (1:1) (60 ml). After centrifuging, the raw product is dissolved in an AcOH/$H_2O$ mixture, deep frozen and then freeze dried.

The residue is recovered in an aqueous solution of 25% acetic acid and then purified by semi-preparative RP-HPLC with a Shimadzu LC-4A system, using a C-18 Hypersil hyperprep column (300 Å, 8 μm, 10×260 mm), at a flow rate of 3 ml.$min^{-1}$, at 50° C. and a detection at 215 nm: system A solvent: 0.05% TFA in deionized water; system B solvent: 0.05% TFA in isopropanol 40% in deionized water (gradient: from 0 to 30% of buffer solution B in 30 minutes, and then from 30 to 40% of buffer solution B in 20 minutes and from 40 to 50% in 50 minutes). The fractions containing the tetraquinoylated tree are collected, deep frozen and then freeze dried. A part of the residue (54 mg) is recovered in a mixture of hydrazine 10% in water (4 ml), for 1 hour at room temperature to permit deprotection of the alcohol functions of the quinoyl residues. The reaction medium is then directly purified under the conditions already described (gradient: from 0 to 20% of buffer solution B in 40 minutes), to provide 15 mg (40%) of the tetra-quinoylated tree in the form of power after freeze drying. ES-MS: m/z$[M+H]^+$ calculated 1369.7; found 1369.8; $[M+Na]^+$ calculated 1391.8; found 1391.7.

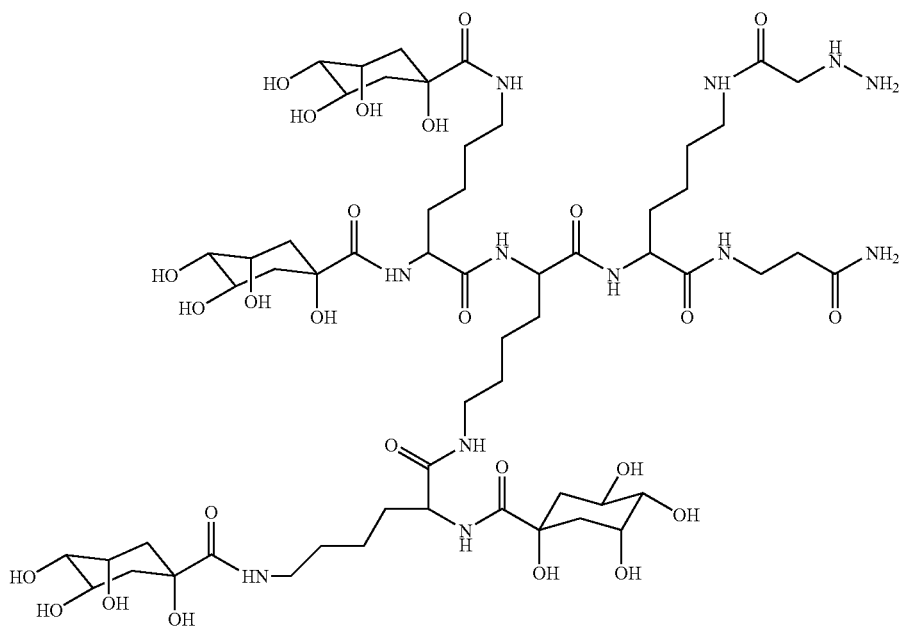

(Qui)₄AKHdz

EXAMPLE 3

Synthesis of Peptides Functionalized by a Group Derived From Hydrazine Having the Formula —CO—CHR'—NH—NH₂, Where R'=H The peptides H₂N—KVGFFKR—NH₂ (SEQ ID NO: 16) (R'=4-aminobutyl) and H₂N—VYKAL-NH₂ (SEQ ID NO: 17) (R'=isopropyl) are solid-phase synthesized on a Rink amide resin AM-PS 1% DVD (0.70 mmol/g, 100-200 mesh, Senn Chemicals AG) using Emoc/tert-butyl chemistry, as described in EXAMPLE 1, §2, on the scale of 0.25 mmole. The syntheses are carried out using an Applied Biosystems 431A automatic synthesizer, with single coupling.

After completing the peptide sequences, the $N^\alpha$ amine functions of lysine and valine are deprotected using a solution of piperadine 20% in NMP. The peptidyl resins are then transformed into hydrazine derivatives in a solid-phase electrophilic N-amination reaction, using N-Boc-3(4-cyanophenyl)oxaziridine —BCPO), as described in the literature (D. BONNET et al., *J. Peptide Res.*, 1999, 54 270 and O. MELNYK et al., *J. Peptide Res.*, 1998, 52, 180).

Briefly, the peptidyl-resins are reacted with 60 mg (0.244 mmole) of BCPO in solution in CH₂Cl₂ (6 ml) for 3 hours. After washing with CH₂Cl₂ and then DMF, the resins are treated with 50 mg (0.25 mmole) of N-benzyl hyrazine in its hydrochlorate form in solution in DMF/AcOH/H₂O (8.5/1/0.5) (5 ml) (3 ×10 minutes). After, washing with DMF and then CH₂Cl₂, the peptidyl-resins are neutralized with a solution of DIEA 5% in CH₂Cl₂ (2 ×2 minutes), and finally washed with CH₂Cl₂. This series of operations is repeated 10 times.

The hydrazinopeptides are deprotected and cloven from the resin using a treatment with 10 ml of a TFA/H₂O/thioanisole/TIS mixture (94/2.5/2.5/1) for 1 hour 30 minutes. The resin is filtered on sintered glass and the peptides are precipitated in 100 ml of a cooled ethyl ether/pentane mixture (1/1). The residues are centrifuged, freeze dried to produce 149 and 133 of raw product, respectively, and then purified by semi-preparative RP-HPLC with a Shimadzu LC-4A system using a C-18 Hypersil hyperprep column (300 Å, 8 µm, 10×260 mm), at a flow rate of 3 ml.min⁻¹, at 50° C. and a detection at 215 nm: system A solvent: 0.05% TFA in deionized water; system B solvent: 0.05% TFA in isopropanol 40% in deionized water.

123 mg (36%) of the compound H₂N—KVGFFKR—NH₂ (SEQ ID NO: 16) are obtained after purification (gradient: from 0 to 70% of buffer solution B in 70 minutes) followed by freeze drying. TOF-PDMS: m/z [M+H]⁺ calculated 895.9; found 895.5.

27.8 mg (13.3%) of the compound H₂N—VYKAL-NH₂ (SEQ ID NO: 17) are obtained after purification (gradient: from 0 to 40% of buffer solution B in 200 minutes) followed by freeze drying. TOF-PDMS: m/z [M+H]⁺ calculated 607.8; found 607.5.

EXAMPLE 4

Synthesis of Lipophilic Vectors (IIIa), (IIIb), III(c) and (IVa) According to the Invention Lipophilic vectors (IIIa) and (IIIb), shown hereinafter, correspond to general formula (III) according to the invention, in which L represents, respectively, a carbon chain having the formula CH₃—(CH₂)₁₄— or the formula CH₃—(CH₂)₇—CH=CH—(CH₂)₇—.

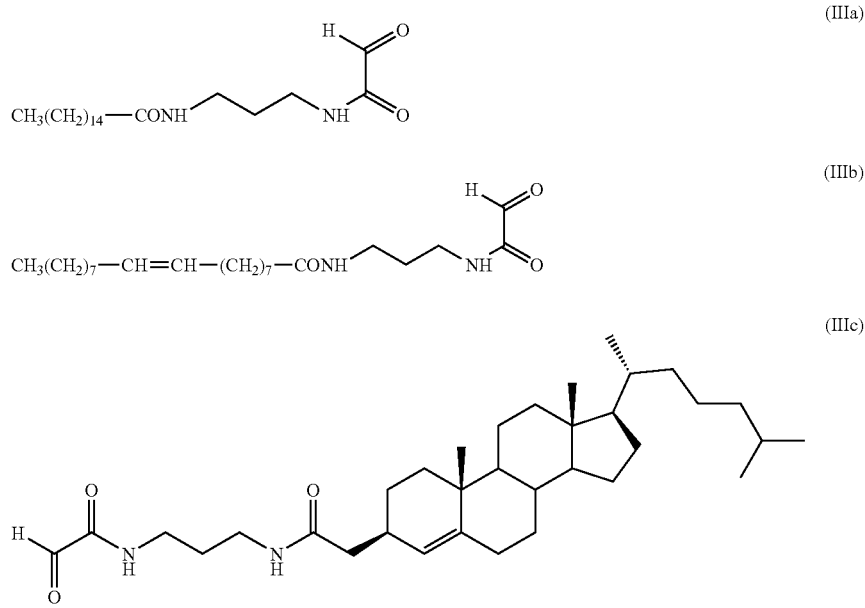

(IIIa)

(IIIb)

(IIIc)

Lipophilic vector (IVa), represented hereinafter, corresponds to general formula (IV) according to the invention, in which L represents a carbon chain having the formula $CH_3-(CH_2)_{14}-$.

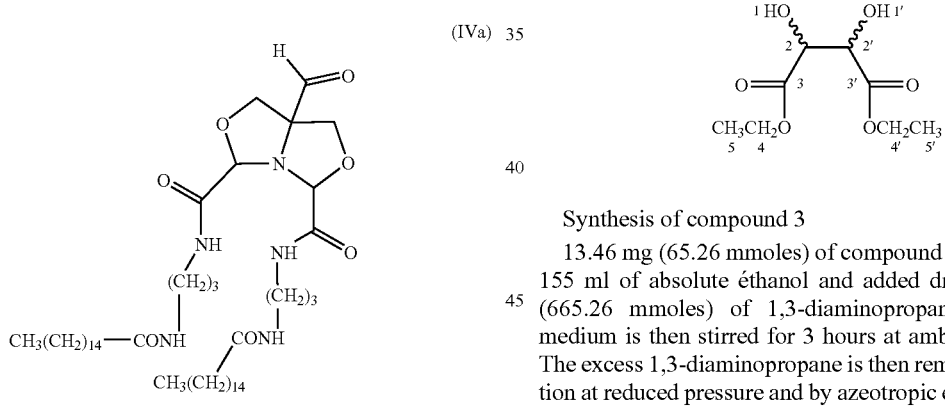

1) Synthesis of Lipophilic Vector (IIIa) (FIG. 1).

Synthesis of compound 2

In a 500 ml flask, 10 g (66.6 mmoles) of tartaric acid 1 are dissolved in 200 ml of absolute ethanol, in the presence of 1% by weight of Amberlyst 15 resin. The flask is provided with a soxhlet system containing 4 A activated molecular sieve. The ethanol is refluxed for 48 hours. The reaction medium is then filtered with n°4 sintered glass to remove the resin. The filtrate is concentrated at reduced pressure and yields a pale yellow oil. Residue 2 is dried overnight on $P_2O_5$ and used without any form of purification (m =13.46 g, yield =98.0%).

Analysis of compound 2, represented below, using thin-layer chromatography, gives a migration index Rf=0.76 in the eluant $CH_2Cl_2/MeOH/H_2O/AcOH$ (90/10/0.1/0.05).

RMN $^1$H (CDCl$_3$): 1.33 (t, 6H, H$_{5,5'}$, J$_{5-4}$=7.2 Hz), 3.28 (s, 2H, H$_{1,1'}$), 4.33 (q, 4H, H$_{4,4'}$, J$_{4-5}$=7.1 Hz), 4.54 (s, 2H, H$_{2,2'}$). RMN $^{13}$C:14.14 (C5,5'), 62.48 (C4,4'), 72.08 (C$_{2,2'}$), 171.62 (C$_{3,3'}$).

Synthesis of compound 3

13.46 mg (65.26 mmoles) of compound 2 are dissolved in 155 ml of absolute éthanol and added dropwise to 56 ml (665.26 mmoles) of 1,3-diaminopropane. The reaction medium is then stirred for 3 hours at ambient temperature. The excess 1,3-diaminopropane is then removed by evaporation at reduced pressure and by azeotropic entrainment in the presence of ethanol (3×200 ml). The yellow oil obtained is dried on $P_2O_5$ overnight, and then recovered in an ethanol/toluene mixture (1/1) and concentrated at reduced pressure (3×200 ml). A yellow compound in the form of a paste is thus obtained. This compound is precipitated in 50 ml of an ethyl ether/ethanol mixture (5/1), and then filtered, and the whitish precipitate is stirred for 1 hour 30 minutes at 0° C. in the presence of ethyl ether. It is then filtered with sintered glass and washed twice cold with the minimum of ethyl ether. Residual solid 3 is dried overnight on $P_2O_5$ (m=13.92 g, yield=81.3%).

The analysis of compound 3 represented below, is as follows : Rf=0.34 in THF/AcOH/H$_2$O/AcO$^-$NH$_4^+$ (35/20/10/1% weight). RMN $^1$H (DMSO-d6): 1,48 (q, 4H, H$_{6\ et\ 6'}$, J$_{6-5,6,7\ et\ 6'-5',6'7'}$=6.65 Hz), 2.51 (m, 4H, H$_{7-7'}$), 3.14 and 3.16 (t, 4H, H$_{5\ et\ 5'}$, J$_{5-6\ et\ 5'-6'}$=6.3 Hz), 4.19 (s, 2H, H$_{2,2'}$), 7.75 (t, 2H, H$_{4,4'}$, J$_{4,4'}$=5.97 Hz). RMN $^{13}$C:33.51 (C$_{6,6'}$), 36.98 (C$_{7,7'}$), 40.06 (C$_{5,5'}$), 73.43 (C$_{2,2'}$), 172.87 (C$_{5,5'}$).

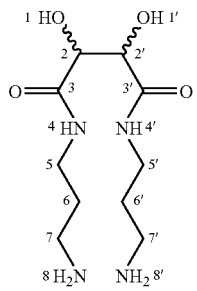

Synthesis of compound (IIIa)

996.9 mg (3.8 mmoles) of compound 3 are dissolved in 15 ml of water. The pH of the solution, which is equal to 8.5, is reduced to 3.25 using 1.46 g of citric acid. 1.06 g (4.9 mmoles) of solid $NaIO_4$ are then added in four steps, for 5 minutes, to the reaction medium kept at room temperature using a water bath. After 10 minutes' stirring, 570 mg of tartaric acid (3.8 mmoles) are added to neutralize the excess $NaIO_4$ that has not reacted. After 10 minutes' stirring at ambient temperature, the pH is adjusted to 8.6 with 24 ml of N-methyl-morpholine. The reaction medium is diluted with 70 ml of 2-methyl-propan-2-ol and 20 ml of water. 2.16 g (1.6 eq.) succinimidyl palmitoate are then added to the solution, which is stirred overnight at room temperature. The pH is then adjusted to 3.5 with 7.11 g of citric acid. The medium is diluted with 40 ml of a solution saturated with NaCl and extracted with 140 ml of dichloromethane, and then 100 ml of chloroform. The organic phase is washed with twice 100 ml of a solution saturated with $KH_2PO_4$, twice 100 ml of a solution saturated with NaCl, and then dried on $Na_2SO_4$, filtered and concentrated at reduced pressure. The residual solid compound is purified on silica using, as an eluent, a $CH_2Cl_2$/AcOEt/EtOH mixture (70/22/5). 951.4 mg of the lipophilic vector (IIIa), i.e. a yield of 42.3%, are thus obtained.

The analysis of compound (IIIa), represented below in its hydrate form, is as follows : RMN $^1$H (DMSO-d6): 0.87 (t, 3H, $H_1$, $J_{1,2}$=5.31 Hz), 1.25 (m, 24H, $H_2$), 1.83 (m, 4H, $H_3$, $H_8$), 2.39 (m, 2H, $H_4$), 3.57 (m, 4H, $H_7$, $H_9$), 4.41 (s, 2H, $H_{14,15}$), 5.50 (m, 1H, $H_{12}$). RMN $^{13}$C:14.31 ($C_1$), 22.96 ($C_2$), 26.35 ($C_8$), 29.99 ($C_3$), 36.79 ($C_4$), 37.14 ($C_7$), 92.18 ($C_{12}$), 173.42 ($C_5$), 175.22 ($C_{11}$). ES-MS:[M+H]$^+$ calculated 387.5; found 387.2.

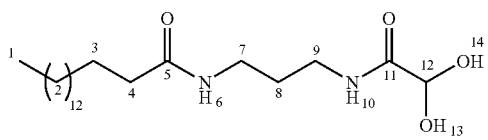

2) Synthesis of Lipophilic Vector (IIIb) (FIG. 1).

Activated oleic acid in the form of N-hydroxy-succinimide ester is first of all prepared from 859 mg (3.0 mmoles) of oleic acid, 353 mg (3.0 mmoles) of N-hydroxysuccinimide and 370 µl (2.3 mmoles) of diisopropylcarbo-diimide, which are dissolved in 30 ml of a THF/$CH_2Cl_2$ mixture (1/1). After remaining overnight at 4° C., the medium is concentrated at reduced pressure and used without any other form of purification for the following part of the synthesis.

Procedure is then as for obtaining lipophilic vector (IIIa), as described above: 500 mg (1.9 mmoles) of compound 3, prepared as indicated previously, are dissolved in 10 ml of water. The pH of the solution, which is equal to 8.5, is adjusted to 3.5 with 667 mg of citric acid. 530 mg (2.4 mmoles) of solid $NaIO_4$ are added in four steps, for 5 minutes, with the medium held at room temperature using a water bath. After 10 minutes' stirring, 286 mg of tartaric acid (1.9 mmoles) are added to neutralize the excess $NaIO_4$. After 10 minutes' stirring, the pH is adjusted to 8.6 with 12 ml of N-methylmorpholine. The medium is diluted with 35 ml of 2methyl-propan-2-ol and 20 ml of water. The activated oleic acid in the form of N-hydroxysuccinimide ester is dissolved in 50 ml of 2-methyl-propan-2-ol and added to the solution. After stirring overnight, the pH of the medium is adjusted to 3.5 with 15 g of citric acid and diluted with 20 ml of a solution saturated with NaCl. The mixture is extracted with 70 ml of $CH_2Cl_2$. The organic phase is washed twice with 50 ml of solution saturated with $KH_2PO_4$, and then twice with 50 ml of a solution saturated with NaCl, dried on $Na_2SO_4$ and concentrated at reduced pressure. The residual solid is purified on silica using as an eluant a $CH_2Cl_2$/AcOEt/EtOH. mixture (70/22/5). 336.3 mg of the lipophilic vector (IIIb), i.e. a yield of 27%, are thus obtained.

3) Synthesis of Lipophilic Vector (IIIc) (FIG. 1).

The synthesis is carried out using N-cholesterylcarbonyloxy-succinimide as described in connection with the preparation of lipophilic vector (IIIa) above. 50.3 mg (0.1905 mmole) of compound 3, prepared as indicated above, are dissolved in 2 ml of water. The pH of the solution, equal to 11.05, is adjusted to 3.08. with 126 mg of citric acid. 53.6 mg (0.248 mmole) of solid $NaIO_4$ are added in 4 operations over a period of 5 minutes, the medium being kept at room temperature using a cold water bath. After 10 minutes' stirring, 24 mg of tartaric acid (0.19 mmole) are added to neutralize the excess $NaIO_4$. After 10 minutes' stirring, the pH is then adjusted to 8.51 with 2.4 ml of N-methylmorpholine. The medium is diluted with 10 ml of 2-methyl-propan-2-ol. 161.1 mg (0.305 mmole) of N-cholesterylcarbonyloxy-succinimide are added in solid form to the solution. After stirring for 1 hour at room temperature, and then for 2 hours at 60° C., 10 ml of $CH_2Cl_2$ are added to completely dissolve the N-cholesterylcarbonyloxy-succinimide. After stirring for 1 hour at room temperature, the pH of the aqueous phase is adjusted to 3.8 with 1.8 g of citric acid. The mixture is extracted with 15 ml of $CH_2Cl_2$. The organic phase is washed twice with 30 ml of solution saturated with $KH_2PO_4$ and then with 30 ml of an NaCl saturated solution (with the addition of 15 ml of ethyl ether to permit separation of the phases). The organic phase is then dried on $Na_2SO_4$ and concentrated at reduced pressure. The residual solid is purified on silica gel using, as an eluent, a $CHCL_3$/AcOH mixture (95/5) to produce 53.4 mg of lipophilic vector (IIIc), i.e. a yield of 32.2%.

Figure 2:
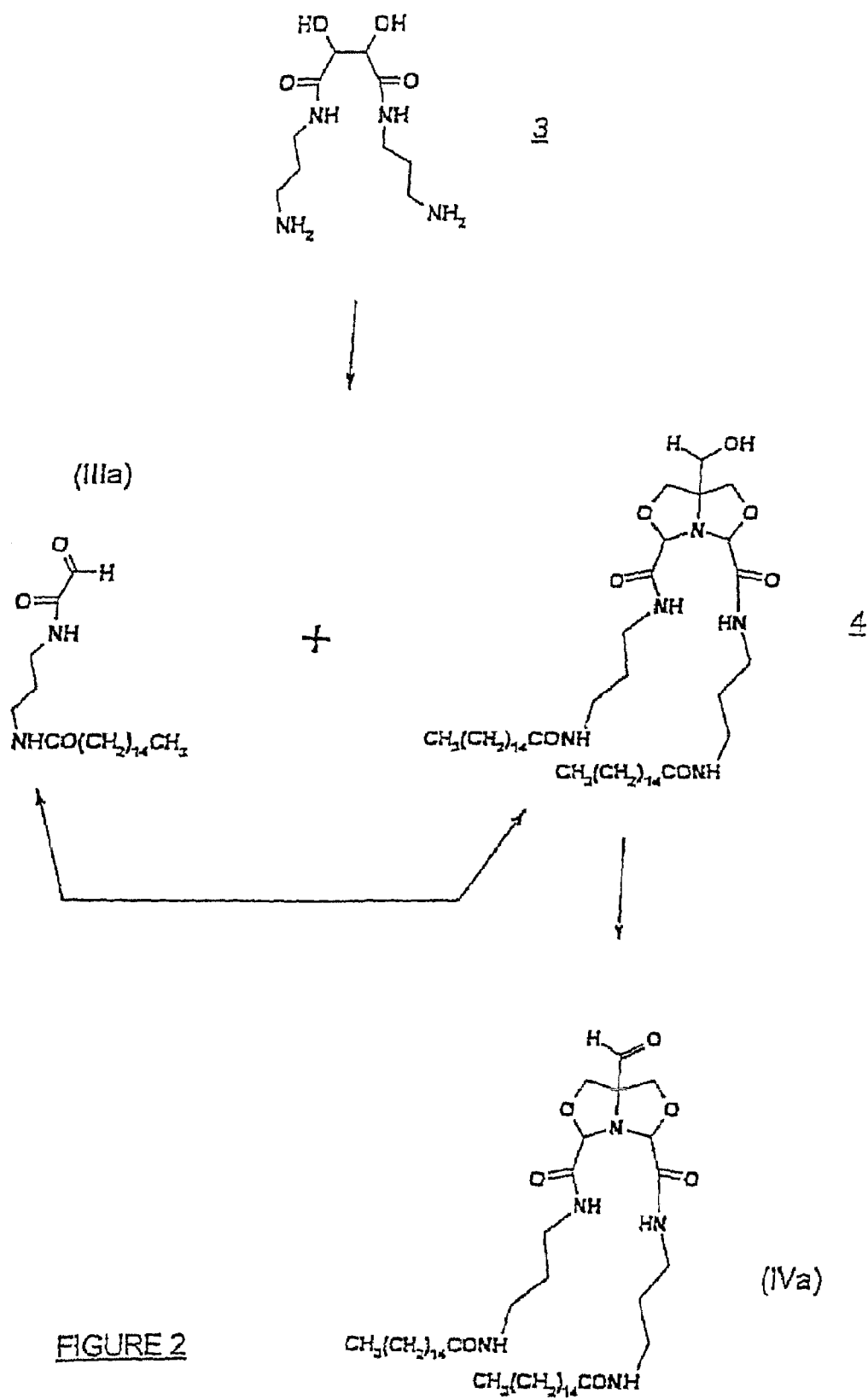
FIG. 2 illustrates another process of synthesis of the lipophilic vector of formula (IIIa), as well as synthesis of the lipophilic vector of formula (IVa) according to the invention.

4) Synthesis of Lipophilic Vector (IVa) (FIG. 2)

1 g (3.8 mmoles) of compound 3, the synthesis of which has been described above, is dissolved in 10 ml of water. The pH is adjusted to 3.25 with citric acid (1.8 g). 1.06 g (4,95 mmoles) of $NaIO_4$ are then added in 4 steps to the reaction medium kept at room temperature using a water bath. Once the addition is completed, the mixture is stirred for 10 minutes. The progress of the reaction is monitored by thin-film chromatography using the THF/AcOH/$H_2O$/AcO$^-NH_4^+$eluent (35/20/10/1% weight).

The excess $NaIO_4$ is consumed by adding 3 eq. of tartaric acid. After 5 minutes' stirring at ambient temperature, the pH of the reaction medium is adjusted to 8.55 by adding 7 g of tris(hydroxymethyl)aminomethane. 70 ml of tert-butanol are added, as well as 1.21 g (3.4 mmoles) of solid succinimidyle palmitoate. The mixture is vigorously stirred overnight, diluted with 50 ml of water saturated with $KH_2PO_4$, and then extracted twice with a $CH_2Cl_2$/tert-butanol mixture (100 ml/50 ml). The organic phase is washed twice with an NaCl-saturated solution and then dried on $MgSO_4$ and concentrated at reduced pressure. The residual paste-like yellow solid is dissolved in ethanol and the solution is concentrated at reduced pressure. The operation is carried out twice in order to remove the residual tert-butanol. There is obtained compound 4, which corresponds to lipophilic vector (IVa) in a reduced form, in the form of a white solid, in a mixture with lipophilic vector (IIIa).

Purification of 301.4 mg of this solid using chromatography on silica with a $CH_2Cl_2$/AcOEt/EtOH mixture (70/20/10) makes it possible to obtain 157.7 mg (yield=52.2%) of compound 4 and 37.6 mg (yield=13.2%) of lipophilic vector (IIIa).

The analysis of compound 4, represented below, is as follows:

NMR$^1$H (pyridine-d5): 0.86 (t, 6H, $H_{1,1'}$, J=6.30 Hz), 1.25 (m, 48H, $H_{2,2'}$), 1.83 (m, 8H, $H_{3,3',8,8'}$), 2.37 (t, 2H, $H_4$, J=7.20 Hz), 2.40 (t, 2H, $H_{4'}$, J=7.20 Hz), 3.60 (m, 8H, $C_{7,7',9,9'}$), 3.99 (s, 2H, $H_{15}$), 4.07 (s, 2H, $H_{13}$), 4.08 (d, 1H, $H_{13'}$, $J_{13'-13''}$=8.70 Hz), 4.48 (d, 1H, $H_{13''}$, $J_{13''-13'}$=8.70 Hz), 5.40 (s, 1H, $H_{12}$), 5.50 (s, 1H, $H_{12'}$), 6.80 (t, 1H, $H_{16}$, J=5.10 Hz), 8.50 and 8.55 (t, 2H, $H_{6,6'}$, $J_{6-7\ or\ 6'-7'}$=5.72 Hz), 8.89 and 9.07 (t, 2H, $H_{10,10'}$, $J_{10-9\ or\ 10'-9'}$=6.16 Hz). NMR $^{13}$C : 15.60 ($C_{1,1'}$), 24.25 ($C_{2,2'}$), 27.58 ($C_{3,3'}$), 31.15 ($C_{8,8'}$), 37.54 ($C_{4,4'}$), 38.02 ($C_{7,7',9,9'}$), 65.29 ($C_{15}$), 74.00 ($C_{13}$), 75.5 ($C_{13'}$), 76.18 ($C_{13''}$), 93.70 and 94.90 ($C_{12}$ or $C_{12'}$), 171.45 ($C_{5,5'}$), 175.29 ($C_{11,11'}$). ES-MS: [M+H]$^+$ calculated 823.2; found 822.7.

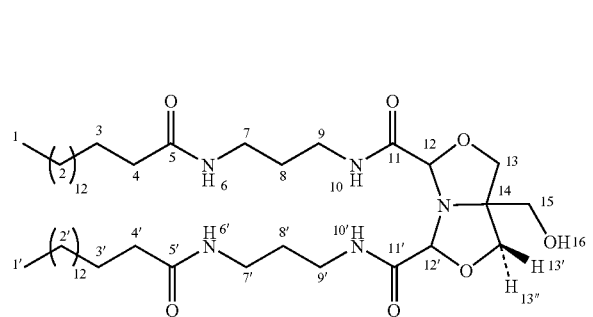

Compound 4 is then oxidized in order to obtain lipophilic vector (IVa): 40 mg (48.6 µmoles) of compound 4 are dissolved in 750 µl of $CH_2Cl_2$ and added to 61.8 mg (145.8 µmoles) of Dess-Martin periodinane (i.e. the compound 1,1,1-triacetoxy-1,1-dihydro-1,2-benziodexol-3(1H)-one, as described in *J. Org. Chem.*, 1983, 48 4156 and in *J. Am. Chem. Soc.*, 1991, 113, 7277) dissolved in 1.5 ml of $CH_2Cl_2$. The mixture is stirred for 18 hours at room temperature. The reaction mixture is then diluted with 10 ml of $CH_2Cl_2$, 10 ml of ethyl ether and 10 ml of a solution saturated with $NaHCO_3$. 46.1 mg of $Na_2S_2O_4$ are then added to the solution. After 5 minutes' stirring, 5 ml of ethyl ether and 5 ml of $CH_2Cl_2$ are added and the two phases are separated. The organic phase is washed twice with 15 ml of a solution saturated with $NaHCO_3$, dried on $MgSO_4$, filtered and concentrated at reduced pressure. The residual yellow oil is purified by chromatography on silica using a $CH_2Cl_2$/AcOEt/EtOH/$Et_3$N mixture (70/20/15/0,5%). 23 mg (57.7%) of lipophilic vector (IVa) are thus obtained.

The analysis of lipophilic vector (IVa), represented below, is as follows : RMN $^1$H (pyridine-d5): 0.87 (t, 6H, $H_{1,1'}$, J=6.30 Hz), 1.26 (m, 48H, $H_{2,2'}$), 1.83 (m, 8H, $H_{3,3',8,8'}$), 2.39 (m, 4H, $H_{4,4'}$), 3.60 (m, 8H, $C_{7,7',9,9'}$), 4.21 (m, 4H, $H_{13,13'}$), 5.60 (m, 2H, $H_{12,12'}$), 8.46 (m, 2H, $H_{6,6'}$), 9.02 (m, 2H, $H_{10,10'}$). RMN $^{13}$C: 14.30 ($C_{1,1'}$), 22.95 ($C_{2,2'}$), 26.32 ($C_{3,3'}$), 29.86 ($C_{8,8'}$), 36.75 ($C_{4,4'}$), 36.75 ($C_{7,7',9,9'}$), 73.5 ($C_{13,13'}$), 93.5 ($C_{12,12'}$), 166.9 ($C_{5,5'}$), 170.7 ($C_{11,11'}$). ES-MS: [M+H]$^+$ calculated 821.2; found 820.6.

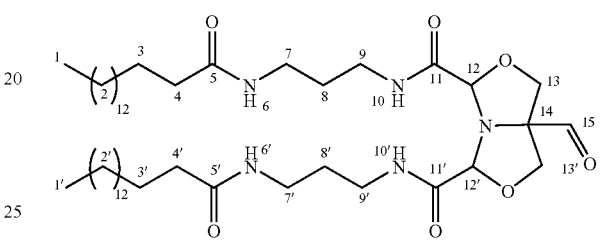

EXAMPLE 5

Another Protocol for Synthesis of Lipophilic Vector (IIIa) (FIG. 2)

As an alternative to the protocols described in example 2, lipophilic vector (IIIa) according to the invention may be synthesized from lipophilic vector (IVa) in a reduced form (i.e. compound 4), according to the following protocol. 245.0 mg of the mixture of lipophilic vector (IIIa) with compound 4, obtained in example 2 before purification are dissolved in a mixture of tert-butanol/$H_2O$/TFA 10% in water (15 ml/10 ml/1 ml). The mixture is stirred overnight at ambient temperature, and then diluted with a solution saturated with NaCl (15 ml). The reaction medium is then extracted twice with a $CH_2Cl_2$/tert-butanol mixture (20 ml/20 ml). The organic phase is washed twice with 15 ml of a solution saturated with NaCl, filtered and concentrated at reduced pressure. The white solid (IIIa) thus obtained is purified by chromatography on silica under the conditions described in example 2 in connection with the obtaining of the lipophilic vector of formula (IIIa). There are thus obtained 136.2 mg of compound (IIIa), i.e. a yield of 56.2%.

EXAMPLE 6

Another Protocol for Synthesis of Lipophilic Vector (IVa) (FIG. 2)

As an alternative to the protocol described in example 2, it is possible to obtain compound 4 i.e. lipophilic vector (IVa), in a reduced form, from lipophilic vector (IIIa), according to the following protocol.

A solution with 242.3 mg/ml of tris(hydroxymethyl)-aminomethane in water is prepared and then adjusted to a pH of 8.5 with concentrated hydrochloric acid. This solution is then saturated with NaCl, after which it is filtered. 20.25 mg (55.0 μmoles) of lipophilic vector (IIIa) dissolved in 600 μl of 2-methyl-propan-2-ol are added to 600 μl of the solution previously prepared. The reaction medium is stirred at ambient temperature for 4 hours and diluted with 2 ml of water, and the product is extracted with 2 ml of a $CH_2Cl_2$/2-methyl-propan-2-ol solution (1/1). The organic phase is washed twice with 1 ml of a solution saturated with $KH_2PO_4$, and then dried on $Na_2SO_4$, filtered and concentrated at reduced pressure. 20.14 mg (54.7 μmoles) of lipophilic vector (IIIa) dissolved in 2 ml of 2-methyl-propan-2-ol are added to the solid residue obtained previously. After 13 hours' stirring at 30° C., the reaction medium is diluted with 4 ml of $CH_2Cl_2$. The organic phase is washed with 2 ml of a solution saturated with NaCl, dried on $Na_2SO_4$, filtered and concentrated at reduced pressure. The solid residue is purified in a silica column using as an eluent the $CH_2Cl_2$/AcOEt/EtOH mixture (70/22/12) to obtain 23.1 mg of compound 4, i.e. a yield of 51%. The latter is then oxidized, as described in example 2, to produce lipophilic vector (IVa).

EXAMPLE 7

Figure 3:
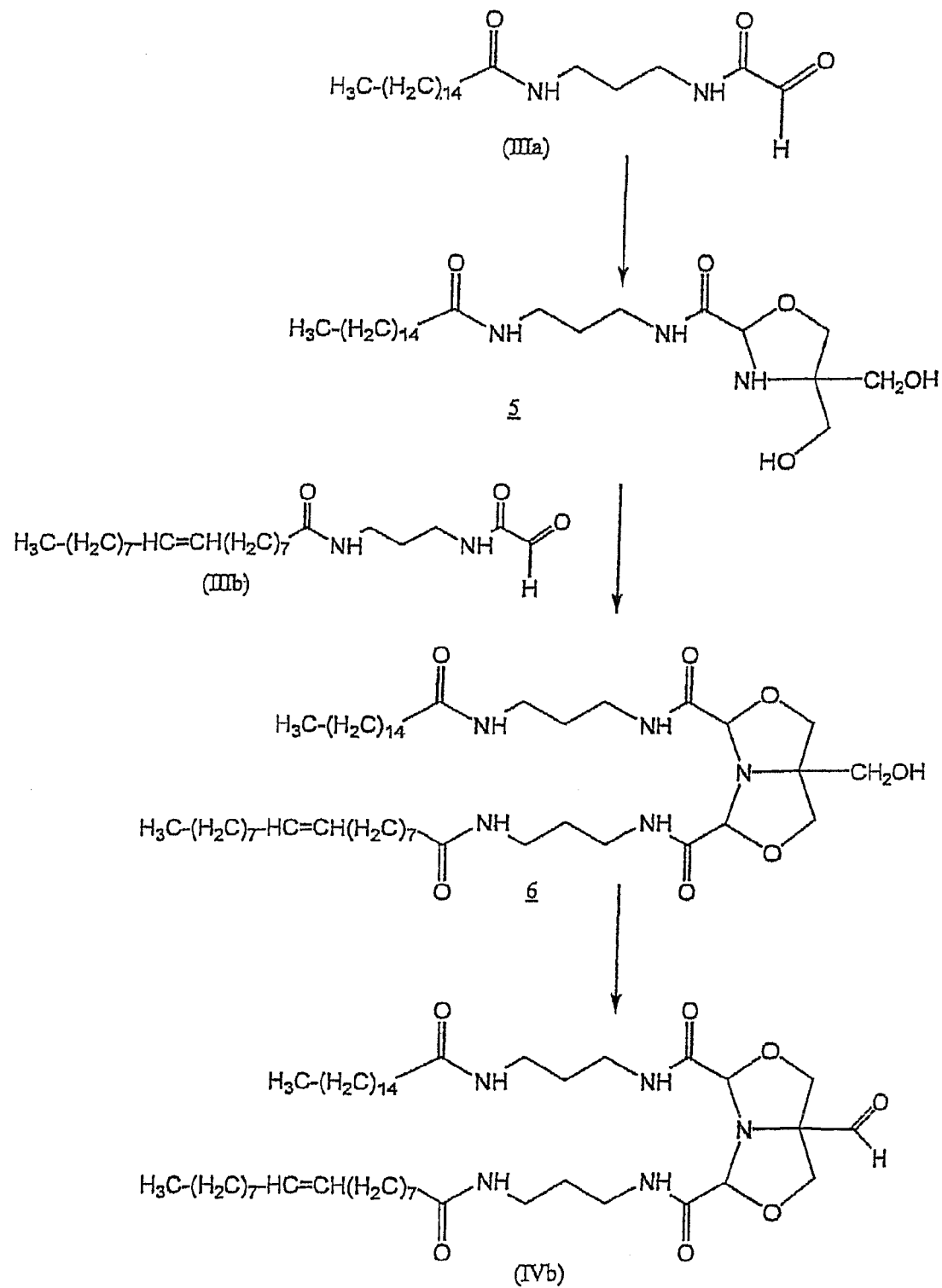
FIG. 3 illustrates the synthesis of the lipophilic vector of formula (IVb) according to the invention.

Synthesis of Lipophilic Vector (IVb) (FIG. 3)

As an alternative to the protocol of synthesis of lipophilic vector (IVa), it is possible to obtain compound 6, i.e. lipophilic vector (IVb) in a reduced form, from lipophilic vectors (IIIa) and (IIIb), according to the following protocol:

A 242.3 mg/ml (2 mol/l) solution of tris(hydroxymethl)-aminomethane in water is prepared and then adjusted to a pH of 8.5 with concentrated hydrochloric acid. This solution is then saturated with NaCl and then filtered. 99.9 mg (270 mmole) of lipophilic vector (IIIa) dissolved in 3 ml of 2-methyl-propan-2-ol are added to 3 ml of the previously prepared solution. The reaction medium is stirred at room temperature for 6 hours, diluted with 5 ml of water and the product is extracted with 5 ml of a solution of $CH_2Cl_2$/2-methyl-propan-2-ol (1/1). The organic phase is washed twice with 2 ml of a solution saturated with $KH_2PO_4$, and then dried on $Na_2SO_4$, filtered and concentrated at reduced pressure to produce palmitoylated oxazolidine 5, in the form of a solid residue.

99.2 mg (270 mmole) of lipophilic vector (IIIb) dissolved in 10 ml of 2methyl-propan-2-ol are then added to intermediary 5, obtained previously. After 20 hours' stirring at 30° C., the reaction medium is diluted with 20 ml of $CH_2Cl_2$. The organic phase is washed with 10 ml of solution saturated with NaCl, dried on $Na_2SO_4$, filtered and concentrated at reduced pressure. The solid residue is purified on silica gel using the $CH_2Cl_2$/AcOEt/EtOH mixture (70/22/12) to obtain 133 mg of compound 6, i.e. a yield of 53%.

Characterization of oxazolidine 5: [1]NMR (300 MHz, $CDCl_3$): δ (ppm): 0.75 (t, 3 H, $J_{1-2}$ =6.7 Hz, H1), 1.25 (m, 24 H, H2), 1.80 (m, 4 H, H3 and H8), 2.33 (t,2 H, $J_{3-4}$ =7.49 Hz, H4), 3.53 (m, 4 H, H7 and H9), 4.04 (s, 2H, H13), 4.20 (s, 4H, H15 and H15'), 4.23 (s, 1 H, H17), 5.41 (s, 1 H, H12), 8.39 (t, 1 H, $J_{6-7}$ =5.7 Hz, H6), 8.99 (t, 1 H, $J_{10-9}$ =5.9 Hz, H10); [13]C (300 MHz, $CDCl_3$): δ (ppm): 14.8 (C1), 26.8 (C3), 30.9 (C8), 23.4, 30.3 and 37.6 (C2), 37.2 (C4, 7,9), 63.9 and 70.8 (C15 and C15'), 64.4 (C13), 68.8 (C14), 90.9 (C12), 171.4 (C5), 174.1 (C11); MALDI-TOF-MS: [M+H+] calculated 471.7; found 471.2.

5

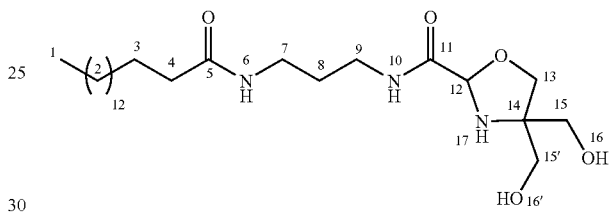

Characterization of bis-oxazolidine 6: NMR [1]H: δ (ppm) 0.84 (m, 6 H, H1 and H1'); 1.23 (m, 42 H, H2 and H2'); 1.78 (m, 8 H, H, H3', H8 and H8'); 2.05 (m, 4 H, H17 and H17'); 2.34 (m, 4 H, H4 and H4'); 3.50 (m, 8 H, H7, H7', H9 and H9'); 3.95 (s, 2 H, H15); 4.03 (s, 2 H, H13); 4.05 (d, 1 H, H13', $J_{13'-13''}$=8.9 Hz); 4.45 (d, 1 H, $H_{13''}$,$J_{13''-13'}$=8.8 Hz); 5.36 (m, 2 H, H18 and H18'); 5.37 and 5.45 (s, 2H, H12 and H12'); 8.35 and 8.45 (t, 2 H, $J_{6-7}$ =5.7 and $J_{6-7'}$=5.9 Hz H6 and H6'); 8.78 and 9.0 (t, 2 H, $J_{10-9}$=6.1 and $J_{10'-9'}$=6.0 Hz, H 10 and H10'); NMR $C^{13}$: δ (ppm) 14.4 (C1 and C1'); 23.1, 29.8 and 32.3 (C2 and C2'); 29.8 (C3 and C3'); 26.4 (C8 and C8'); 27.6 (C17 and C17'); 36.8 (C4 and C4'); 36.4 and 36.7 (C7, C7', C9 and C9'); 64.1 (C15 and C15'); 72.6 (C13); 74.3 and 75.0 (C13'and C13''); 92.6 and 93.8 (C12 and C12'); 130.3 (C18 and C18'); 166.9, 170.3, 173.8 and 174.1 (C5, C5', C10, C10'). MALDI-TOF-MS: [M+H+]: calculated 849.3; found 848.6.

6

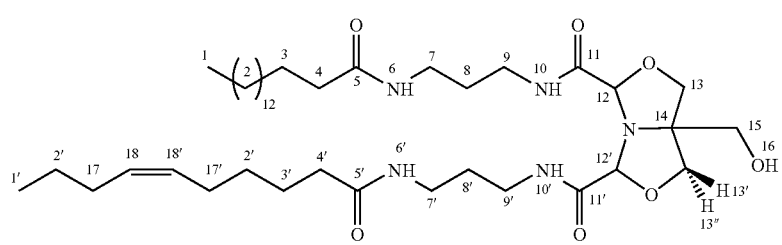

The latter is oxidized, as described in Example 2, to produce lipophilic vector (IVb): MALDI-TOF-MS: [M+H$^{30}$] calculated 847.2; found 846.6.

EXAMPLE 8

Couplings, in Solution, Between One or More Peptides and a Non-peptides Type Lipophilic Vector Bearing an Aldehyde Function 1) Coupling the Mixture of Peptides SIV1-7 and TT with lipophilic vector (IIIa) (FIG. 3).

The mixture of hydrazinopeptides SIV1-7 and TT, prepared in accordance with example 1, is made from approximately 2 mg of each freeze dried product. A solution of lipophilic vector (IIIa), prepared in accordance with example 2 or example 3, in a quantity of 1.1 equivalents in relation to the total of the hydrazinoacetic functions borne by the peptides (taking into account the counter-ions and the peptide content of each freeze dried product) in the tert-butanol is prepared. The coupling reaction (chemical ligation) takes place in a tert-butanol/water mixture (95/5 by volume), the final peptide concentration being in the order of 1.3 mmol/l. The deionized water is first added to the mixture of hydrazinopeptides so as to wet them, the solution of lipophilic vector (IIIa) in the tert-butanol then being added.

The ligation reaction leads to the production of the mixture of lipopeptides 7, with the term <<sequence>> (FIG. 3) denoting the peptide sequence of peptides SIV1-7 or TT. This reaction is followed by RP-HPLC as follows. 20 μl of the reaction medium are taken; to these are added 80 μl of an acetic acid/water mixture (20/80). 50 μl of this volume are injected on an analytical C3 column (Zorbax, 4.6 mm in diameter, 300 mm long) with a solvent B gradient (such as the one described in example 1 in connection with the purification of peptides SIV1-7 and TT) from 0 to 100% in 30 minutes (1 ml/min, 215 nm, 50° C.). This technique makes it possible to monitor the conversion of the hydrazinopeptides into peptides ligated on the same chromatogram, the hydrazinopeptides and the peptides chemically linked to the lipophilic vector ("ligated" peptides) not having the same elution times. The ratio of the sum of the integrations of the peaks of the hydrazinopeptides and the ligated peptides makes it possible to estimate the conversion rate of the reaction.

After approximately 20 hours' coupling reaction, fractions of the reaction medium are freeze dried and an LC-MS analysis of the lipopeptides in the mixture is carried out. For this purpose, the Hewlett-Parckard HPLC system is connected, via a capillary tube, to a Micromass Quatro mass spectrometer. HPLC conditions are the same as those used for monitoring the coupling reaction, the flow rate used being, however, 0.2 ml/min on a C3 column (Zorbax, 2.1 mm in diameter, 200 mm long). The mixture of the hydrazinopeptides alone (1 mg/ml aqueous solution) is injected in a proportion of 20 μl with a gradient of 0 to 100% in solvent B, for 30 minutes. The exit order of the hydrazinopeptides, their retention times (rt, in minutes) and their observed molecular weights are as follows: TT (17.1; 222); SIV5 (17.5 ; 3452) SIV2 (18.3; 2968); SIV1 (19.4; 3258); SIV6. (20.9; 3501.5); SIV7 (21.0; 4804); SIV4 (21.2; 3186); SIV3 (21.6; 3112).

The coupling reaction is stopped after about 20 hours and the reaction medium, freeze dried, is replaced in solution in water in a proportion of 1 mg/ml. This solution is injected under the same conditions as those described above in the case of the peptide mixture, except for a more resolvent gradient ranging from 0 to 50% in solvent B for 10 minutes, and then from 50 to 100% for 30 minutes, followed by a few minutes at 100%. At this stage, it is always possible to detect the presence of hydrazinopeptides SIV1-7 and TT using HPLC and LC-MS. They are, however, partly masked by the background noise and impurities that accumulate during the first part of the gradient in solvent B. Five majoroity peaks are observed using HPLC, with, in parallel, six TIC (Total Ion Count) peaks observed with LC-MS. These peaks correspond to SIV1-7 and TT coupled to lipophilic vector (IIIa), some of which co-elute. It is possible, however, to determine their order of exit and their observed weights, as indicated in Table II.

TABLE II

|  | [M + H]$^+$ calculated | [M + H]$^+$ observed | rt (minutes) (LC/MS) |
|---|---|---|---|
| SIV1 | 3608.89 | 3608 | 19.4 |
| SIV5 | 3803.716 | 3802 | 19.6 |
| TT | 2572.57 | 2572 | 19.9 |
| SIV2 | 3319.35 | 3318 | 20.4 |
| SIV7 | 5156.5 | 5155 | 21.2 |
| SIV4 | 3538.465 | 3538 | 23.1 |
| SIV6 | 3852.9 | 3851.5 | 23.1 |
| SIV3 | 3463.49 | 3462 | 24.5 |

2) Coupling Peptide Mu-IFNγ with Two Lipophilic Vectors (IIIa) (FIG. 5).

708.2 μg (1.92 μmoles) of lipophilic vector (IIIa), prepared according to example 2 or example 3, dissolved in 640 μl of tert-butanol, are added to 5.04 mg (i.e. approximately 1 μmole) of peptide Mu-IFNγ, prepared according to example 1, previously placed in suspension in 35 μl of water. After 5 hours' stirring at room temperature, the reaction medium is frozen and freeze dried. The analysis for resulting lipopeptide 8 using ES-MS is as follows: [M+H]$^+$ calculated 5547.7, found 5547.5.

3) Coupling Peptides Mu-IFNγ a and Mu-IFNγ b with Lipophilic Vector (IIIa).

1.067 mg of lipophilic vector (IIIa) dissolved in 1.88 ml of tert-butanol are added to 10 mg of peptide (i.e. either peptide Mu-IFNγ a, or peptide Mu-IFNγ b) in 105 μl of water. After 4 hours at room temperature, the solution is diluted with the same volume of water and freeze dried. There are obtained 9.2 mg of lipopeptide from Mu-IFNγ a (a lipopeptide referred to as <<L-Mu-IFNγ a >>) and 9.3 mg of lipopeptide from Mu-IFNγ b (a lipopeptide referred to as <<L-Mu-IFNγ b>>). Their analysis using ES-MS is as follows: L-Mu-IFNγ a: [M+H]$^+$ calculated 3008.7; found 3007.5. L-Mu-IFNγ b: [M+H]$^+$ calculated 3008.7; found 3007.0.

4) Coupling of Peptides Mu-IFNγ c, Mu-IFNγ d. Mu-IFNγ a and Mu-IFNγ b with Lipophilic Vector (IIIc)

5.8 mg of lipophilic vector (IIIc) are dissolved in 6.302 ml of 2methyl-propan-2-ol.

To 5 mg (1.32 μmol) of peptide (i.e. either peptide Mu-IFNγ a or peptide Mu-IFNγ b) dissolved in 50 μl of water are added 965 μl (1.58 μmol) of the solution containing lipophilic vector (IIIc) prepared above. After 5 hours' reaction at room temperature, the solution is diluted with the same volume of water and freeze dried. There are obtained 6.3 mg of lipopeptide from Mu-IFNγ a (the lipopeptide named Cho-Mu-IFNγ a) and 6.4 mg of lipopeptide from Mu-IFNγ b (the lipopeptide named Cho-Mu-IFNγ b). Their analysis using MALDI-TOF-MS is as follows:

Cho-Mu-IFNγ a: m/z(M+H)$^+$ calculated 3184.0: found 3183.2

Cho-Mu-IFNγ b: m/z(M+H)$^+$ calculated 3184.0; found 3184.3.

In the same way, to 8 mg (1.30 µmol) of peptide (i.e. either peptide Mu-IFNγ c or peptide Mu-IFNγ d) dissolved in 50 µl of water are added 952 µl of the solution containing lipophilic vector (IIIc). After 5 hours' reaction at room temperature, the solution is diluted with the same volume of water and freeze dried. There are obtained 8.6 mg of lipopeptide from Mu-IFNγ c [the lipopeptide named Cho-Mu-IFNγ c or 9 FIG. 7)] and 8.4 mg of lipopeptide from Mu-IFNγ d (the lipopeptide named Cho-Mu-IFNγ d). Their analysis using MALDI-TOF-MS is as follows:

Cho-Mu-IFNγ c: m/z $(M+H)^+$ calculated 5298.4; found 5298.0

Cho-Mu-IFNγ d: m/z $(M+H)^+$ calculated 5298.4; found 5299.7.

5) Coupling Peptide G18R with Lipophilic Vector (IIIb).

15 mg (6.75 µmoles) of peptide are soaked with 254 µl of water, and then 3.73 mg of lipophilic vector (IIIa) in solution in 4.82ml of tert-butanol are added. After 48 hours at room temperature, the solution is freeze dried. There are obtained 17 mg of lipopeptide 6 the TOF-PDMS analysis of which is as follows : $[M+H]^+$ calculated 2259.8, found 2259.4.

Figure 6:
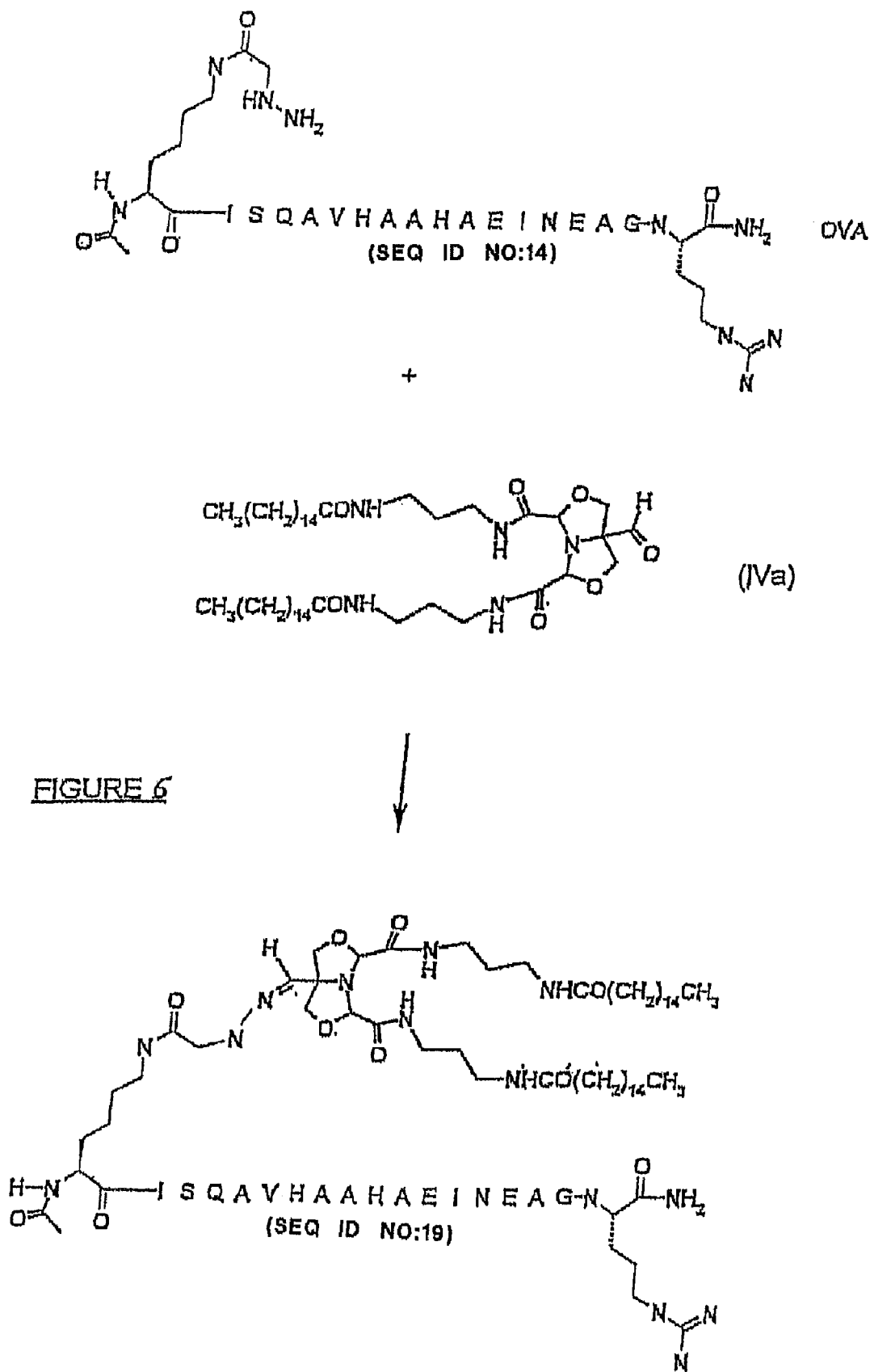
FIG. 6 illustrates the coupling, using the process according to the invention, of the peptide referred to as OVA (SEQ ID NO: 14) with a lipophilic vector of formula (IVa).

6) Coupling of Peptide OVA with Lipophilic Vector (IVa) (FIG. 6).

1 mg (0.40 µmoles) of peptide OVA, prepared in accordance with example 1, is dissolved in 75 µl of a 25 mM phosphate/citrate buffer solution, with a pH of 6.2. This buffer solution is obtained using 160.5 µl of a solution of $Na_2HPO_4$ 0.2M and 89.5 µl of citric acid 0.1M, the mixture being topped up to 1 ml with water. 663 µg (0.81 µmoles) of lipophilic vector (IVa), prepared in accordance with example 2 or example 6, are dissolved in 75 µl of tert-butanol. The two solutions are then mixed and heated at 50° C. for 5 h. The progress of the reaction is monitored using HPLC on a Zorbax C3 column using a linear gradient of 0 to 100% of solvent B constituted by a mixture of 80% acetonitrile/20% TEAP, 25 mM, pH 7.1 for 30 minutes, and then 10 minutes at 100% in solvent B (flow rate: 1 ml/min, detection at 215 nm). Aprés 5 hours, lipopeptide 10 is precipitated by adding 500 µl of water, centrifuged and recovered in 500 µl of isopropanol. The raw lipopopeptide is analysed using ES-MS : $[M+H]^+$ calculated 2818.4; found 2818.6.

7) Coupling of Glycomimetic [(Qui)$_4$AKDhz] with Lipophilic Vector 9.4 mg (6.4 mmol) of compound [(Qui)$_4$AKDhz] are dissolved in 244 ml of water and then added to 2.44 mg of lipophilic vector (IIIa) in solution in 5.07 ml of 2-methyl-propan-2-ol. The reaction medium is stirred for 5 hours at 30° C. and then diluted with water, deep frozen and freeze dried to provide, quantitatively, the derivative QuiAK-Pam in the form of a white residue.

MALDI-TOF: m/z $(M+Na)^+$ calculated 1742.0; found 1742.9; $(M+K)^+$ calculated 1758.1; found 1757.9 (Qui)$_4$AK-Pam.

8) Coupling of the Mixture of Peptides SIV1-7, TT and (Qui)$_4$AKDhz with Lipophilic Vector (IIIa)

The protocol observed is the one described in EXAMPLE 8, 1).

52.5 mg of an equimass mixture of each of peptides SIV1-7 (corresponding to a mean value of 12.1 mmoles of each of the peptides, taking into account the counter-ions and the peptide content of each freeze dried product) are dissolved in 0.464 ml of water. In parallel, 12.94 mg (8.72 mmoles) of compound (Qui)$_4$AKDhz are dissolved in 0.335 ml of water. To the two solutions, previously combined, are added 9.63 mg 24.9 mmoles, 1.2 equivalents) of lipophilic vector (IIIa) in solution in 15.198 ml of 2-methyl-propan-2-ol. The final concentration of each of the peptides is thus approximately 1.3 mol.l$^{-1}$ in a 2-methyl-propan-2-ol/$H_2O$ mixture (95/5). The reaction medium becomes clear immediately. The latter is stirred in a nitrogen atmosphere at 30° C. Monitoring with RP-HPLC [used as described in 1)] of the progress of the reaction informs us that the ligations are almost complete after only 5 minutes. After 5 hours, the reaction medium is diluted with water, deep frozen and then freeze dried. A micro-preparative RP-HPLC is applied to a sample of the raw reaction product to permit identification of each of the lipopeptides by mass spectrometry analysis.

| | $[M + H]^+$ calculated | $[M + H]^+$ observed | Parent peptide fragment |
|---|---|---|---|
| SIV1 | 3623.9 | 3625.4 | 3276.0 |
| SIV5 | 3803.7 | 3803.2 | 3453.9 |
| SIV2 | 3319.3 | 3319.0 | 2969.7 |
| SIV7 | 5156.5 | ? | ? |
| SIV4 | 3538.5 | ? | 3188.8 |
| SIV6 | 3852.9 | ? | 3503.9 |
| SIV3 | 3463.5 | 3464.2 | 3113.9 |
| QuiAK-Pam | 1742.0[a] | 1742.0[a] | |

[a]in the form of a sodium adduct

9) Coupling between compounds H$_2$N—KVGFFKR—NH$_2$ (SEQ ID NO: 16)— and H$_2$N—VYKAL —NH$_2$ (SEQ ID NO: 17) and lipophilic vector (IIIa)

1.73 mg (4.5 mmoles) and 0.68 (1.8 mmoles) of lipophilic vector (IIIa) are dissolved in 3.60 and 1.41 ml of 2-methyl-propan-2-ol, respectively, and then added to 5.8 mg (4.3 mmoles) of compound H$_2$N—KVGFFKR —NH$_2$ (SEQ ID NO: 16) dissolved in 190 ml of H$_2$O and to 1.4 mg (1.07 mmoles) of compound H$_2$N—VYKAL-NH$_2$ (SEQ ID NO: 17) dissolved in 77 ml of H$_2$O, respectively. The reaction media are stirred for 5 hours at 30° C. and then diluted with water, deep frozen and freeze dried to provide compounds 11 and 12, respectively.

4.5 mg (66 mg) of compound 13 are obtained after semi-preparative RP-HPLC purification with a Shimadzu LC-4A system, using a Zorbax C3 column, at a flow rate of 3 ml min$^{-1}$, at 60° C. and detection at 215 nm: system A solvent: 0.05% TFA in deionized water; system B solvent: 0.05% TFA in isopropanol 60% in deionized water (gradient: from 20 to 40% of buffer solution B in 10 minutes and then isocratic in 10 minutes, and then from 40% to 100% in 10 minutes, and isocratic for 20 minutes) followed by freeze drying. MALDI-TOF-MS: m/z $[M+H]^+$ calculated 1245.7; found 1245.8; [M+Na]+calculated 1267.7; found 1267.8.

Characterization of compound 11: MALDI-TOF-MS: m/z $[M+H]^+$ calculated 957.3; found 957.8; $[M+Na]^+$ calculated 979.3; found 979.7.

EXAMPLE 9

Analysis and Quantification f the Expression of Molecules of Class II of the Major Histocompatibility Complex (MHC), at the Surface of the Cells, Induced by Incubation of These Cells with Lipopeptides According to the Invention 1) Lipopeptides Used.

The lipopeptides according to the invention that are used in these experiments are lipopeptides L-Mu-IFNγ a and L-Mu-IFNγ b, the synthesis of which is described in paragraph 3 of example 5 above. As mentioned in paragraph 3 of example 1 above, peptide Mu-IFNγ a corresponds to the 20 amino acids contiguous with the C-terminal end of murine interferon-γ

(IFN-γ). Peptide Mu-IFNγ b is a <<scramble>> sequence of the sequence present in peptide Mu-IFNγ a, i.e. a sequence in which the amino acids (their order in the sequence) were mixed.

Lipopeptide L-mIFNγ 95-132 is described in the article by K. THIAM et al. published in *J. Med. Chem.*, 1999, 42, 3732-3736. It is the result of the coupling of a palmitoyl residue, borne by a lysine, at the N-terminal end of sequence 95-132 corresponding to the 38 amino acids contiguous with the C-terminal end of murine interferon-γ. The coupling of the lipophilic part on the peptide sequence is described in the aforementioned article by K. THIAM et al: it results from the introduction, in solid phase, of compound Fmoc-Lys(palmitoyl)—OH. The lipopeptide thus obtained is then deprotected and separated from the solid support.

Lipopeptide SL-mIFNγ 95-132 is also described in the aforementioned article by K. THIAM et al.: this is a <<scramble>> version of lipopeptide L-mIFNγ 95-132.

Lipopeptide L-mIFNγ 113-132 is also described in the aforementioned article by K. THIAM et al.: this lipopeptide includes the same peptide sequence as lipopeptide L-Mu-IFNγ a according to the invention, but the palmitoyl residue is not introduced in the same way as in the case of lipopeptide L-Mu-IFNγ a, and the bond between the peptide sequence and the lipophilic part is not the same in the two lipopeptides (amide bond between the palmitic acid and the amine function of the side chain of a lysine in the case of L-mIFNγ 113-132, the lipopeptide being solid-phase synthesized, whereas a hydrazone bond and coupling in solution are involved in the case of L-Mu-IFNγ a).

2) Protocol for Quantification of the Expression of Molecules of Class II of the Major Histocompatibility Complex (MHC) at the Surface of the Cells.

The COLO 205 cells (human cell line obtained from a carcinoma of the colon) come from the ATCC (American Type Culture Collection) cell bank. They are cultivated in an RPMI 1640 medium (Gibco BRL, Courbevoie, France) with 10% of fetal calf serum (FCS) and 5 mM of sodium pyruvate, and incubated at 37° C. in the presence of 5% of $CO_2$. The cells are stimulated for 24 hours with different concentrations (35, 42 or 50 μM) of lipopeptides. The cells are then marked for 1 hour with 10 μl of class II DR anti-HLA antibodies, coupled with FITC (clone TAL, 1B5, Cymbus Biotechnology Ltd., Hants, Great Britain) (results shown in Table IIIa), or the L243 antibody revealed by a second antibody coupled to ALEXA 488 (Molecular Probe, Netherland) (results shown in Table IIIb).

The surface expression of the class II molecules of the MHC is analysed using flow cytometry with a Coulter EPICS II cytometer, at the rate of 10,000 events per sample. The fluorescence intensity observed is directly proportional to the quantity of class II molecules of the MHC present on the surface of the cells. The mean fluorescence value observed for the non-treated cells and for the treated cells ("Mean" column in Table III) makes it possible to calculate a ratio between the mean fluorescence value of the non-treated cells and the mean fluorescence value for the treated cells ("Ratio" column in Table III). The control consists in incubating the cells in the absence of lipopeptides.

3) Results.

The results obtained during two independent experience series are presented in Table IIIa and IIIb.

TABLE IIIa

| Name of Product | 35 μM | | 42 μM | | 50 μM | |
| --- | --- | --- | --- | --- | --- | --- |
| | Mean | Ratio | Mean | Ratio | Mean | Ratio |
| control | 0.726 | | | | | |
| L-mIFNγ 95-132 | 7.94 | 10.9 | 6.94 | 9.55 | 10.3 | 14.1 |
| SL-mIFNγ 95-132 | 2.23 | 3.07 | 2.30 | 3.16 | 2.69 | 3.70 |
| L-Mu-IFNγ a | 11.1 | 15.2 | 16.7 | 23.0 | 19.5 | 26.8 |
| L-Mu-IFNγ b | 3.44 | 4.73 | 5.26 | 7.24 | 7.79 | 10.7 |
| L-mIFNγ 113-132 | 13.2 | 18.18 | 16.1 | 22.1 | 14.6 | 20.11 |

TABLE IIIb

| Name of the product | 5 μM | | 10 μM | | 35 μM | |
| --- | --- | --- | --- | --- | --- | --- |
| | Mean | Ratio | Mean | Ratio | Mean | Ratio |
| control | 0.607 | | | | | |
| L-MU-IFNγa | 0.99 | 1.6 | 1.51 | 2.48 | 5.85 | 9.6 |
| L-MU-IFNγb | 0.76 | 1.25 | 0.99 | 1.63 | 1.65 | 2.71 |
| L-MU-IFNγc | 1.3 | 2.14 | 1.72 | 2.83 | 15.1 | 24.8 |
| L-MU-IFNγd | 1.39 | 2.28 | 2.36 | 3.88 | 7.31 | 12.0 |
| Cho-MU-IFNγa | 2.04 | 3.4 | 2.81 | 4.6 | 36.9 | 60.7 |
| Cho-MU-IFNγb | 0.95 | 1.56 | 1.88 | 3.1 | 11.6 | 19.1 |
| Cho-MU-IFNγc | 2.95 | 4.8 | 4.27 | 7.03 | 21.6 | 35.5 |
| Cho-MU-IFNγd | 2.02 | 3.32 | 2 | 3.3 | 1.56 | 2.57 |

In Table IIIa, comparison between the results obtained for L-Mu-IFNγ a and for L-mIFNγ 113-132 (lipopeptides of the same size, including the same peptide sequence but differing from one another in the nature of the bond between the lipophilic part and the peptide sequence) at 42 μM and at 50 μM shows that the expression of the class II molecules of the MHC at the surface of the cells is greater when the cells have been incubated with the lipopeptide according to the invention.

In Table IIIb, the comparison between the results obtained with the product L-Mu-IFNγ a also described in Table IIIa and the derivatives comprising a lipophilic part derived from cholesterol Cho-Mu-IFNγ a-d shows that the expression of the class II molecules at the surface of the cells is even stronger when the cells have been incubated with derivatives of the cholesterol than with derivatives of the palmitic acid.

Passage through the membranes of the lipopeptides according to the invention is thus more efficient, given the nature of the bond between the lipophilic part and the peptide sequence (hydrazone bond).

These results show that the lipopeptides according to the invention are capable of passing through the membranes of cells more efficiently than the lipopeptides of the prior art. The lipopeptides according to the invention are thus suitable for vectorization of active principles in the cells.

As emerges from the above, the invention is in no way limited to those of its implementations, embodiments and modes of application that have just been described more explicitly; on the contrary, it encompasses all variants that may occur to a man skilled in the art, without departing from the framework, or the scope, of the present invention. In particular, the coupling process that has been described could be used to anchor peptides to lipophilic surfaces including lipophilic vectors according to the present invention, or to supra-molecular systems, such as lipidic bilayers, liposomes or multilamellar particles.

The invention claimed is:

1. A process for coupling, in solution, between at least one peptide compound and at least one lipophilic vector bearing an aldehyde function, said coupling including a step of forming a hydrazone bond between said peptide compound and said lipophilic vector, wherein said lipophilic vector is of a non-peptide type and corresponds to the following formula (I):

$$[(R^1)(R^2)_i]D—CHO \quad (I)$$

wherein:
i represents 0 or 1,
if i is equal to 0, D represents a bond,
if i is equal to 1, D represents a mono- or polycyclic saturated, unsaturated or aromatic heterocycle, and
$R^1$ and $R^2$, which may be identical or different, each represent a group having the formula L-f-E-f' where L represents a residue of a lipid, B represents a spacer arm, and f and f' represent functions binding, respectively, L to E and B to D.

2. The process according to claim 1, comprising the following steps:
a) preparation of at least one completely deprotected peptide compound bearing, either at its N-terminal end, or at the end of the side chain of a lysine or an ornithine possibly present at some point in the peptide sequence, 1 to 4 hydrazine derivative groups having the formula —CO—CHR'—NR—NH$_2$, where R and R' represent, independently of one another, a hydrogen atom or a ramified or cyclic, linear, saturated or unsaturated alkyl group, including from 1 to 10 carbon atoms, as well as, possibly, 1 to 3 heteroatoms chosen from oxygen, sulfur, and nitrogen and substitutable by 1 to 6 groups chosen from the hydroxy, alkoxy, aryloxy, amino, aminoalkyl, aminoaryl, thio, thioalkyl, carbonyl, guanadino and carboxamido groups;
b) reaction, in solution, of said peptide compound(s) obtained in step a) with at least one lipophilic vector of a non-peptide type of formula (I) as defined in claim 1, bearing an aldehyde function.

3. The process according to claim 2, wherein the reaction carried out in step b) is carried out in a mixture of water and of at least one water-miscible lipophilic solvent.

4. The process according to claim 3, wherein said water-miscible lipophilic solvent is tert-butanol.

5. The process according to claim 2, wherein said hydrazine derivative groups are α-hydrazinoacetic groups.

6. The process according to claim 1, wherein said peptide compound is selected from the group consisting of peptides and peptide derivatives.

7. The process according to claim 6, wherein said peptide derivatives are selected from the group consisting of glycopeptides, pseudopeptides and dendrimeric glycomimetics of a peptide type.

8. The process according to claim 7, wherein said dendrimeric glycomimetics of a peptide type correspond to formula (II):

$$(B^2M)_m(XN)_nA \quad (II)$$

wherein:
$B^2$ corresponds to one or more general formulae (a) or (b) hereinafter:

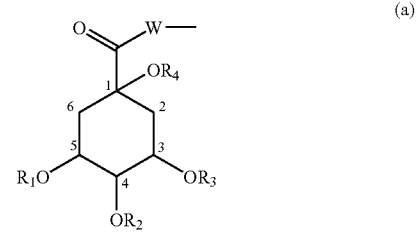

(a)

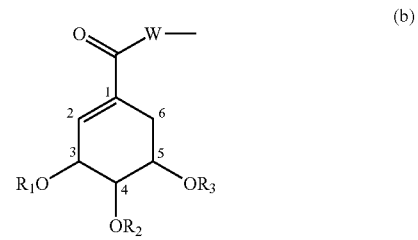

(b)

where $R_1$, $R_2$, $R_3$ and $R_4$ represent, independently of one another, a hydrogen atom or a protective group, and where W represents a bond or a saturated or unsaturated, ramified or cyclic linear carbon chain, including 1 to 18 carbon atoms and possibly 1 to 12 atoms chosen from oxygen, sulfur, and nitrogen, said carbon chain possibly being substituted by 1 to 16 halogen atoms, X represents the residue of an oligopeptide X' including 1 to 6 amino acids, A represents the residue of an at least tri-functional A' compound, m is an integer between 1 and 32, n is an integer between 0 and 32, and M and N each represent a linkage between $B^2$ and A when n=0 or $B^2$ and X when n is other than 0, and between X and A when n is other than 0, respectively, and include, independently of one another, a function selected from the group consisting of oxime, hydrazone, amide, ester, thioester, hydrazide, hydroxamate, ether, thioether, amine, carbonate, carbamate, thiocarbonate, thiocarbamate, urea, thiourea and thiazolidine functions.

9. The process according to claim 8, wherein compound A' includes a chain of identical or different amino acids selected from the group consisting of lysine, hydroxylysine, serine, threonine, cysteine, ornithine, aspartic acid and glutamic acid.

10. The process according to claim 8, wherein the compound having formula (II) is such that m is an integer of between 4 and 16, n is an integer of between 2 and 8, X represents the residue of an oligopeptide including 2 to 4 residues of amino acids, whereas A represents the residue of a chain including 2 to 8 residues of lysine and taking the form of a dendrimer.

11. The process according to claim 8, wherein the compound having formula (II) is such that $B^2$ represents a residue of one or more compounds chosen from (−)-shikimic acid and (−)-quinic acid.

12. The process according to claim 1, wherein a plurality of different peptide compounds are coupled to a plurality of different lipophulic vectors.

13. The process according to claim 2, wherein said peptide compounds comprise at least one dendrimeric glycomimetic having the general formula (II) and at least one member selected from the group consisting of peptides, glycopeptides and pseudopeptides, and wherein formula (II) is:

$$(B^2M)_m(XN)_nA \quad (II)$$

wherein:

$B^2$ corresponds to one or more general formulae (a) or (b) hereinafter:

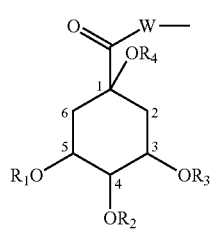

(a)

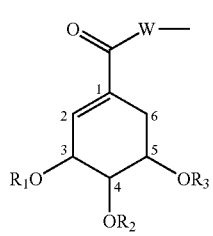

(b)

where $R_1$, $R_2$, $R_3$ and $R_4$ represent, independently of one another, a hydrogen atom or a protective group, and where W represents a bond or a saturated or unsaturated, ramified or cyclic linear carbon chain, including 1 to 18 carbon atoms and possibly 1 to 12 atoms chosen from oxygen, sulfur, and nitrogen, said carbon chain possibly being substituted by 1 to 16 halogen atoms, X represents the residue of an oligopeptide X' including 1 to 6 amino acids, A represents the residue of an at least tri-functional A' compound, m is an integer between 1 and 32, n is an integer between 0 and 32, and M and N each represent a linkage between $B^2$ and A when n=0 or $B^2$ and X when n is other than 0, and between X and A when n is other than 0, respectively, and include, independently of one another, a function selected from the group consisting of oxime, hydrazone, amide, ester, thioester, hydrazide, hydroxamate, ether, thioether, amine, carbonate, carbamate, thiocarbonate, thiocarbamate, urea, thiourea and thiazolidine functions.

14. A lipophilic vector, wherein said vector corresponds to formula (I):

$$[(R^1)(R^2)_i]D-CHO \quad (I)$$

wherein:

i represents 0 or 1, if i is equal to 0, D represents a bond, if i is equal to 1, D represents a mono- or polycyclic saturated, unsaturated or aromatic heterocycle, and $R^1$ and $R^2$, which may be identical or different, each represent a group having the formula L-f-E-f' where L represents a residue of a lipid, E represents a spacer arm, and f represents a —CO—NH— or —CO—O— bond and f' represents a —NH—CO— or —O—CO— bond, and wherein said f bond links L to B and said f' bond links E to D.

15. The lipophilic vector according to claim 14, wherein i is equal to 1 and D represents the heterocycle 1-aza-3,7-dioxabicyclo (3.3.0)-octane.

16. The lipophilic vector according to claim 14, wherein L represents a sterol, a sterol derivative or a linear or ramified, saturated or unsaturated carbon chain, including between 4 and 30 carbon atoms.

17. The lipophilic vector according to claim 16, wherein said sterol derivative is a cholesterol derivative and said carbon chain corresponds to the formula $CH_3-(CH_2)_{14}-$ or $CH_3-(CH_2)_7-CH=CH-(CH_2)_7-$.

18. The lipophilic vector according to claim 14, wherein E represents a saturated or unsaturated, ramified or cyclic linear carbon chain, comprising 1 to 18 carbon atoms and, possibly, 1 to 16 heteroatoms and/or 1 to 7 groups selected from the group consisting of carbonyl groups, heterocycles, heteroaryls, carbocycles and aryls.

19. The lipophilic vector according to claim 18, wherein E is substituted by 1 to 8 hydroxyl or amino groups and/or 1 to 16 halogen atoms.

20. The lipophilic vector according to claim 14, wherein said vector corresponds to formula (III) or to formula (IV):

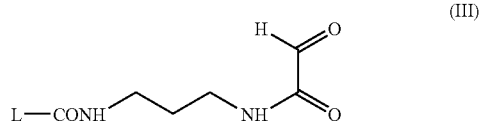

(III)

-continued

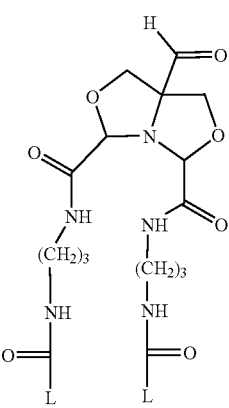

(IV)

in which L represents a residue of a lipid.

21. The lipophilic vector according to claim 20, wherein L represents a carbon chain having the formula $CH_3—(CH_2)_{14}—$ in formulae (III) and (IV).

22. The lipophilic vector according to claim 20, wherein L represents a carbon chain having the formula $CH_3—(CH_2)_7—CH=CH—(CH_2)7—$ in formula (III).

23. The lipopeptide prepared by the coupling process as defined in claim 1, wherein said lipopeptide is comprised of at least one peptide compound bound, by a hydrazone bond, to at least one lipophilic vector of a non-peptide type of formula (I) as defined in claim 1.

24. A mixture of several different lipopeptides as defined in claim 23.

25. The process according to claim 1, wherein said lipopeptide is comprised of at least one peptide compound bound to at least one lipophilic vector of a non-peptide type according to formula (I) of claim 1, and wherein said lipopeptide targets specific cells and/or receptors.

26. The process according to claim 1, wherein the coupling of said peptide compound and said lipophilic vector yields a drug comprising at least one active principle of a peptide type vectorized by at least one lipophilic compound useful for cell targeting.

27. The lipophilic vector according to claim 20, wherein L represents a sterol; a sterol derivative; a cholesterol derivative, a linear or ramified, saturated or unsaturated, carbon chain including between 4 and 30 carbon atoms or a carbon chain that corresponds to the formula $CH_3—(CH_2)_{14}—$ or $CH_3—(CH_2)_7—CH=CH—(CH_2)_7$.

* * * * *

UNITED STATES PATENT AND TRADEMARK OFFICE
CERTIFICATE OF CORRECTION

PATENT NO. : 7,390,875 B2  
APPLICATION NO. : 10/380094  
DATED : June 24, 2008  
INVENTOR(S) : Dominique Bonnet et al.

It is certified that error appears in the above-identified patent and that said Letters Patent is hereby corrected as shown below:

On the Title Page item 73

The line reading "Assignee: Institut Pasteur de Lille, Lille Cedex (FR)" should read --Assignee: Institut Pasteur de Lille, Lille Cedex (FR); Centre National De La Recheche Scientifique CRNS, Paris Cedex (FR).--

Signed and Sealed this

Twenty-sixth Day of May, 2009

JOHN DOLL  
*Acting Director of the United States Patent and Trademark Office*

UNITED STATES PATENT AND TRADEMARK OFFICE
CERTIFICATE OF CORRECTION

PATENT NO. : 7,390,875 B2
APPLICATION NO. : 10/380094
DATED : June 24, 2008
INVENTOR(S) : Dominique Bonnet et al.

It is certified that error appears in the above-identified patent and that said Letters Patent is hereby corrected as shown below:

On the Title Page item 73

The line reading "Assignee: Institut Pasteur de Lille, Lille Cedex (FR)" should read --Assignee: Institut Pasteur de Lille, Lille Cedex (FR); Centre National De La Recherche Scientifique CNRS, Paris Cedex (FR).--

This certificate supersedes the Certificate of Correction issued May 26, 2009.

Signed and Sealed this

Ninth Day of February, 2010

David J. Kappos
*Director of the United States Patent and Trademark Office*

SEQUENCE LISTING

<160> NUMBER OF SEQ ID NOS: 15

<210> SEQ ID NO 1
<211> LENGTH: 27
<212> TYPE: PRT
<213> ORGANISM: Artificial Sequence
<220> FEATURE:
<223> OTHER INFORMATION: SYNTHETIC PEPTIDE SIV1

<400> SEQUENCE: 1

Lys Lys Glu Lys Ile Phe His Ser Met Asp Ile Ala Leu Lys Tyr Thr
 1               5                  10                  15

Met Ala Arg Leu Pro Val Lys Pro Arg Val Ser
             20                  25

<210> SEQ ID NO 2
<211> LENGTH: 24
<212> TYPE: PRT
<213> ORGANISM: Artificial Sequence
<220> FEATURE:
<223> OTHER INFORMATION: SYNTHETIC PEPTIDE SIV2

<400> SEQUENCE: 2

Lys Glu Leu Tyr Met Asp Leu Ile Arg His Arg Arg Ala Ser Tyr Tyr
 1               5                  10                  15

Ile Gly Glu Leu Gly Gly Lys Glu
             20

<210> SEQ ID NO 3
<211> LENGTH: 25
<212> TYPE: PRT
<213> ORGANISM: Artificial Sequence
<220> FEATURE:
<223> OTHER INFORMATION: SYNTHETIC PEPTIDE SIV3

<400> SEQUENCE: 3

Lys Val Leu Lys Trp Leu Trp Gly Phe Thr Lys Pro Tyr Arg Ile Gly
 1               5                  10                  15

Pro Gly Ser Thr Tyr Asp Gln Trp Asp
             20                  25

<210> SEQ ID NO 4
<211> LENGTH: 26
<212> TYPE: PRT
<213> ORGANISM: Artificial Sequence
<220> FEATURE:
<223> OTHER INFORMATION: SYNTHETIC PEPTIDE SIV4

<400> SEQUENCE: 4

Lys Ala Glu Tyr Thr Tyr Ala Leu Thr Pro Asp Phe Lys Trp Ala leu
 1               5                  10                  15

Val Glu Gly Trp Pro Asp Asp Trp Lys Ser
             20                  25

<210> SEQ ID NO 5
<211> LENGTH: 28
<212> TYPE: PRT
<213> ORGANISM: Artificial Sequence
<220> FEATURE:
<223> OTHER INFORMATION: SYNTHETIC PEPTIDE SIV5

<400> SEQUENCE: 5

Lys Gly Glu Glu Leu Arg Lys Arg Gln Cys Ala Gln Ser Ala Glu leu
 1               5                  10                  15

-continued

```
Glu Glu Pro Tyr Arg Ala Tyr Ala Glu Tyr Thr Tyr
            20                  25

<210> SEQ ID NO 6
<211> LENGTH: 32
<212> TYPE: PRT
<213> ORGANISM: Artificial Sequence
<220> FEATURE:
<223> OTHER INFORMATION: SYNTHETIC PEPTIDE SIV6

<400> SEQUENCE: 6

Lys Asp Gly Val Cys Asn leu Met Gln Asn Ile Asp Tyr pro Thr
 1               5                  10                  15

Cys Gly Glu Ser Leu Ala Gln Phe Gly Pro Val Val Glu Ala Gly
                20                  25                  30

Phe Lys

<210> SEQ ID NO 7
<211> LENGTH: 38
<212> TYPE: PRT
<213> ORGANISM: Artificial Sequence
<220> FEATURE:
<223> OTHER INFORMATION: SYNTHETIC PEPTIDE SIV7

<400> SEQUENCE: 7

Lys Asn Thr Pro Asn Tyr Met Arg Val Cys Lys Gln Leu Gly Leu Gln
 1               5                  10                  15

Ile Trp Arg Arg Tyr Ile Asn Gly Val Pro Ile Pro Asn Gln Gln Arg
                20                  25                  30

Tyr Met Trp Gln Ile Gln
            35

<210> SEQ ID NO 8
<211> LENGTH: 18
<212> TYPE: PRT
<213> ORGANISM: Artificial Sequence
<220> FEATURE:
<223> OTHER INFORMATION: SYNTHETIC PEPTIDE TT

<400> SEQUENCE: 8

Lys Lys Lys Leu Glu Thr Ile Gly Ile Phe Lys Ser Asn Ala Lys Ile
 1               5                  10                  15

Tyr Gln

<210> SEQ ID NO 9
<211> LENGTH: 39
<212> TYPE: PRT
<213> ORGANISM: Artificial Sequence
<220> FEATURE:
<223> OTHER INFORMATION: SYNTHETIC PEPTIDE Mu-IFNy

<400> SEQUENCE: 9

Arg Ser Arg Lys Arg Lys Arg Leu Ser Ser Glu Pro Leu Leu Gln His
 1               5                  10                  15

Val Val Arg Ile Leu Glu Asn Phe Ala Gln Arg Gln Val Gln Pro Asn
                20                  25                  30

Asn Val Glu Phe Lys Ala Lys
            35

<210> SEQ ID NO 10
<211> LENGTH: 21
<212> TYPE: PRT
```

-continued

```
<213> ORGANISM: Artificial Sequence
<220> FEATURE:
<223> OTHER INFORMATION: SYNTHETIC PEPTIDE Mu-IFNya

<400> SEQUENCE: 10

Arg Ser Arg Lys Arg Lys Arg Leu Ser Ser Glu Phe Leu Leu Gln His
 1               5                  10                  15

Val Val Arg Ile Lys
            20

<210> SEQ ID NO 11
<211> LENGTH: 21
<212> TYPE: PRT
<213> ORGANISM: Artificial Sequence
<220> FEATURE:
<223> OTHER INFORMATION: SYNTHETIC PEPTIDE Mu-IFNyb

<400> SEQUENCE: 11

Leu Lys Ser Lys Val Arg Ile Pro Arg Val Lys Gln His Arg Arg
 1               5                  10                  15

Glu Ser Arg Leu Ser Lys
            20

<210> SEQ ID NO 12
<211> LENGTH: 39
<212> TYPE: PRT
<213> ORGANISM: Artificial Sequence
<220> FEATURE:
<223> OTHER INFORMATION: SYNTHETIC PEPTIDE Mu-IFNyc

<400> SEQUENCE: 12

Lys Ala Lys Phe Glu Val Asn Asn Pro Gln Val Gln Arg Gln Ala Phe
 1               5                  10                  15

Asn Glu Leu Ile Arg Val Val His Gln Leu Leu Pro Glu Ser Ser Leu
            20                  25                  30

Arg Lys Arg Lys Arg Ser Arg
            35

<210> SEQ ID NO 13
<211> LENGTH: 39
<212> TYPE: PRT
<213> ORGANISM: Artificial Sequence
<220> FEATURE:
<223> OTHER INFORMATION: SYNTHETIC PEPTIDE Mu-IFNyd

<400> SEQUENCE: 13

Phe Pro Leu Ser Gln Asn Arg Phe Ala Leu Arg Glu Val Arg His Lys
 1               5                  10                  15

Gln Glu Arg Arg Leu Val Val Ser Leu Lys Gln Ile Lys Val Ala
            20                  25                  30

Asn Gln Asn Glu Arg Ser Pro Phe
            35

<210> SEQ ID NO 14
<211> LENGTH: 18
<212> TYPE: PRT
<213> ORGANISM: Artificial Sequence
<220> FEATURE:
<223> OTHER INFORMATION: SYNTHETIC PEPTIDE OVA

<400> SEQUENCE: 14

Arg Gly Ala Glu Asn Ile Glu Ala His Ala Ala His Val Ala Gln Ser
 1               5                  10                  15
```

```
Ile Lys

<210> SEQ ID NO 15
<211> LENGTH: 19
<212> TYPE: PRT
<213> ORGANISM: Artificial Sequence
<220> FEATURE:
<223> OTHER INFORMATION: SYNTHETIC PEPTIDE G18R

<400> SEQUENCE: 15

Arg Ser Met Ala Ser Gly Leu Met Tyr Gly Gly Leu Gly Gly Val Val
 1               5                  10                  15

Ala Gly Lys
```